(12) United States Patent
Love et al.

(10) Patent No.: US 11,571,341 B2
(45) Date of Patent: Feb. 7, 2023

(54) ABSORBENT ARTICLES AND METHODS OF MANUFACTURING THE SAME

(71) Applicant: Medline Industries, LP, Northfield, IL (US)

(72) Inventors: Daniel B. Love, Libertyville, IL (US); Amin Setoodeh, Kildeer, IL (US); Bridget Donovan, Chicago, IL (US); Christopher J. Nelson, Hiram, GA (US); William Rovero, Douglasville, GA (US)

(73) Assignee: Medline Industries, LP, Northfield, IL (US)

( * ) Notice: Subject to any disclaimer, the term of this patent is extended or adjusted under 35 U.S.C. 154(b) by 1124 days.

(21) Appl. No.: 16/181,240

(22) Filed: Nov. 5, 2018

(65) Prior Publication Data

US 2019/0133840 A1 May 9, 2019

Related U.S. Application Data

(63) Continuation of application No. 13/832,965, filed on Mar. 15, 2013, now Pat. No. 10,117,792, which is a (Continued)

(51) Int. Cl.
*A61F 13/15* (2006.01)
*A61F 13/49* (2006.01)
(Continued)

(52) U.S. Cl.
CPC ........ *A61F 13/49* (2013.01); *A61F 13/49012* (2013.01); *A61F 13/49058* (2013.01); *A61F 13/536* (2013.01); *A61F 13/8405* (2013.01)

(58) Field of Classification Search
CPC ................ A61F 13/49; A61F 13/49012; A61F 13/49058; A61F 13/536; A61F 13/8405
See application file for complete search history.

(56) References Cited

U.S. PATENT DOCUMENTS 688,143 A   12/1901 Windle
1,614,239 A   1/1927 Hammond
(Continued)

FOREIGN PATENT DOCUMENTS

DE   102005048868 A1   4/2007
DE   102009059886 A1   10/2010
(Continued)

OTHER PUBLICATIONS

Essity Hygiene and Health Aktiebolag, Notice of Opposition to European Patent No. 2629730, filed in the European Patent Office Jun. 6, 2019.
(Continued)

*Primary Examiner* — Jacqueline F Stephens
(74) *Attorney, Agent, or Firm* — Gurr Brande & Spendlove, PLLC.; Robert Dan Spendlove

(57) ABSTRACT

An absorbent article includes a chassis having a substantially rectangular shape a first portion, a second portion and a crotch portion extending between the first and second portion, a portion of the chassis being configured to absorb fluids. The absorbent article includes a first securement portion operatively coupled to the first portion of the chassis. The absorbent article includes a second securement portion operatively coupled to the second portion of the chassis and configured to releasably attach to the first securement portion. The chassis is configured to include one of a first chassis length or a second chassis length. When the chassis includes the first length, the chassis includes a first width and the first securement portion includes a second width, and when the chassis includes the second length, the chassis includes the first width and the first securement portion includes a third width, greater than the second width.

21 Claims, 21 Drawing Sheets

Related U.S. Application Data continuation-in-part of application No. 13/276,843, filed on Oct. 19, 2011, now Pat. No. 9,439,811.

(60) Provisional application No. 61/394,758, filed on Oct. 19, 2010.

(51) Int. Cl.
*A61F 13/84* (2006.01)
*A61F 13/536* (2006.01)

(56) References Cited

U.S. PATENT DOCUMENTS

| | | |
|---|---|---|
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,612,055 A | 10/1971 | Mesek et al. |
| 3,692,618 A | 9/1972 | Carduck et al. |
| 3,802,817 A | 4/1974 | Matsuki et al. |
| 3,849,241 A | 11/1974 | Harding et al. |
| 3,860,003 A | 1/1975 | Buell |
| 3,955,575 A | 5/1976 | Okuda |
| 3,994,486 A | 11/1976 | Nystrand |
| 4,050,462 A | 9/1977 | Woon et al. |
| 4,051,853 A | 10/1977 | Egan, Jr. |
| 4,055,180 A | 10/1977 | Karami |
| 4,084,592 A | 4/1978 | Tritsch |
| 4,145,763 A | 3/1979 | Abrams et al. |
| 4,195,634 A | 4/1980 | Disalvo et al. |
| 4,205,679 A | 6/1980 | Repke et al. |
| 4,246,900 A | 1/1981 | Schroder |
| 4,251,643 A | 2/1981 | Harada et al. |
| 4,253,461 A | 3/1981 | Strickland et al. |
| 4,296,750 A | 10/1981 | Woon et al. |
| 4,317,449 A | 3/1982 | Novakoski |
| 4,333,466 A | 6/1982 | Matthews |
| 4,340,563 A | 7/1982 | Appel et al. |
| 4,381,781 A | 5/1983 | Sciaraffa et al. |
| 4,402,690 A | 9/1983 | Redfern |
| 4,410,324 A | 10/1983 | Sabee |
| 4,413,996 A | 11/1983 | Taylor |
| D272,190 S | 1/1984 | Sneider |
| 4,490,147 A | 12/1984 | Peirce et al. |
| 4,500,316 A | 2/1985 | Damico |
| 4,516,976 A | 5/1985 | Bell |
| 4,560,381 A | 12/1985 | Southwell |
| 4,596,568 A | 6/1986 | Flug |
| 4,610,680 A | 9/1986 | Lafleur |
| 4,610,682 A | 9/1986 | Kopp |
| 4,615,695 A | 10/1986 | Cooper |
| 4,639,254 A | 1/1987 | Legault et al. |
| 4,643,932 A | 2/1987 | Daniels |
| 4,662,875 A | 5/1987 | Hirotsu et al. |
| 4,663,220 A | 5/1987 | Wisneski et al. |
| 4,699,621 A | 5/1987 | Wisneski et al. |
| 4,670,012 A | 6/1987 | Johnson |
| 4,673,402 A | 6/1987 | Weisman et al. |
| 4,680,012 A | 7/1987 | Morley et al. |
| 4,695,278 A | 9/1987 | Lawson |
| 4,699,620 A | 10/1987 | Bernardin |
| 4,699,622 A | 10/1987 | Toussant et al. |
| 4,704,116 A | 11/1987 | Enloe |
| 4,710,190 A | 12/1987 | Wood et al. |
| 4,720,415 A | 1/1988 | Vander Wielen |
| 4,753,649 A | 6/1988 | Pazdernik |
| 4,758,241 A | 7/1988 | Papajohn |
| 4,770,656 A | 9/1988 | Proxmire et al. |
| 4,770,657 A | 9/1988 | Ellis |
| 4,798,603 A | 1/1989 | Meyer et al. |
| 4,834,735 A | 5/1989 | Alemany et al. |
| 4,834,738 A | 5/1989 | Kielpikowski |
| 4,838,885 A | 6/1989 | Bernardin |
| 4,869,724 A | 9/1989 | Scripps |
| 4,883,480 A | 11/1989 | Huffman et al. |
| 4,884,323 A | 12/1989 | Provost et al. |
| 4,911,702 A | 3/1990 | O'Leary et al. |
| 4,916,005 A | 4/1990 | Loppert et al. |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A * | 7/1990 | Van Gompel ......... A61F 5/4401 604/385.22 |
| 4,963,140 A | 10/1990 | Robertson et al. |
| 4,964,860 A | 10/1990 | Gipson et al. |
| 4,988,344 A | 1/1991 | Reising et al. |
| 4,988,345 A | 1/1991 | Reising et al. |
| 5,013,382 A | 5/1991 | Nalowaniec et al. |
| 5,019,063 A | 5/1991 | Marsan et al. |
| 5,019,072 A | 5/1991 | Polski |
| 5,019,073 A | 5/1991 | Roessler et al. |
| 5,024,672 A | 6/1991 | Widlund |
| 5,026,446 A | 6/1991 | Johnson et al. |
| 5,034,008 A | 7/1991 | Breitkoph |
| 5,046,272 A | 9/1991 | Vogt et al. |
| 5,047,023 A | 9/1991 | Berg |
| 5,055,103 A | 10/1991 | Nomura et al. |
| 5,061,259 A | 10/1991 | Goldman et al. |
| 5,061,262 A | 10/1991 | Chen et al. |
| 5,062,838 A | 11/1991 | Nalowaniec et al. |
| 5,069,678 A | 12/1991 | Yamamoto et al. |
| 5,087,253 A | 2/1992 | Cooper |
| 5,104,116 A | 4/1992 | Pohjola |
| 5,106,385 A | 4/1992 | Allen et al. |
| 5,108,384 A | 4/1992 | Goulait |
| 5,128,193 A | 7/1992 | Anapol et al. |
| 5,133,707 A | 7/1992 | Rogers et al. |
| 5,134,007 A | 7/1992 | Reising et al. |
| 5,147,343 A | 9/1992 | Kellenberger |
| 5,147,347 A | 9/1992 | Huang |
| 5,149,334 A | 9/1992 | Lahman et al. |
| 5,149,335 A | 9/1992 | Kellenberger et al. |
| 5,151,092 A | 9/1992 | Buell et al. |
| 5,156,793 A | 10/1992 | Buell et al. |
| 5,156,902 A | 10/1992 | Pieper et al. |
| 5,163,932 A | 11/1992 | Nomura et al. |
| 5,176,670 A | 1/1993 | Roessler et al. |
| 5,176,671 A | 1/1993 | Roessler et al. |
| 5,188,627 A | 1/1993 | Igaue et al. |
| 5,188,624 A | 2/1993 | Young, Sr. et al. |
| 5,192,506 A | 3/1993 | Kureshy et al. |
| 5,219,646 A | 7/1993 | Gallegher et al. |
| 5,224,405 A | 7/1993 | Pohjola |
| 5,226,992 A | 7/1993 | Morman |
| 5,234,422 A | 8/1993 | Sneller et al. |
| 5,235,515 A | 8/1993 | Ungpiyakul et al. |
| 5,236,429 A | 8/1993 | Widlund |
| 5,242,436 A | 9/1993 | Weil et al. |
| 5,246,433 A | 9/1993 | Hasse et al. |
| 5,248,309 A | 9/1993 | Serbiak et al. |
| 5,263,949 A | 11/1993 | Karami et al. |
| 5,275,590 A | 1/1994 | Huffman et al. |
| 5,279,604 A | 1/1994 | Robertson et al. |
| 5,286,543 A | 2/1994 | Ungpiyakul et al. |
| 5,288,546 A | 2/1994 | Roessler et al. |
| 5,294,478 A | 3/1994 | Wanek et al. |
| 5,295,998 A | 3/1994 | Muckenfuhs et al. |
| 5,300,057 A | 4/1994 | Miller et al. |
| 5,304,161 A | 4/1994 | Noel et al. |
| 5,304,162 A | 4/1994 | Kuen |
| 5,318,555 A | 6/1994 | Siebers et al. |
| 5,320,531 A | 6/1994 | Delizo-Madamba |
| 5,326,612 A | 7/1994 | Goulait |
| 5,330,458 A | 7/1994 | Buell et al. |
| 5,344,691 A | 9/1994 | Hanschen et al. |
| 5,348,547 A | 9/1994 | Payne et al. |
| 5,350,370 A | 9/1994 | Jackson et al. |
| 5,358,500 A | 10/1994 | Lavon |
| 5,364,382 A | 11/1994 | Latimer et al. |
| 5,370,634 A | 12/1994 | Ando et al. |
| 5,370,639 A | 12/1994 | Widlund |
| 5,383,872 A | 1/1995 | Roessler et al. |

(56) References Cited

U.S. PATENT DOCUMENTS

| | | |
|---|---|---|
| 5,387,208 A | 2/1995 | Ashton et al. |
| 5,399,219 A | 3/1995 | Roessler et al. |
| 5,403,302 A | 4/1995 | Roessler et al. |
| 5,411,497 A | 5/1995 | Tanzer et al. |
| 5,422,172 A | 6/1995 | Wu |
| 5,423,789 A | 6/1995 | Kuen |
| 5,425,725 A | 6/1995 | Tanzer et al. |
| 5,433,715 A | 7/1995 | Tanzer et al. |
| 5,439,458 A | 8/1995 | Noel et al. |
| 5,458,592 A | 10/1995 | Abuto et al. |
| 5,460,622 A | 10/1995 | Dragoo et al. |
| 5,462,541 A | 10/1995 | Bruemmer et al. |
| 5,466,513 A | 11/1995 | Wanek et al. |
| 5,486,167 A | 1/1996 | Dragoo et al. |
| 5,489,282 A | 2/1996 | Zehner et al. |
| 5,490,846 A | 2/1996 | Ellis et al. |
| 5,496,298 A | 3/1996 | Kuepper et al. |
| 5,496,428 A | 3/1996 | Sageser et al. |
| 5,501,679 A | 3/1996 | Krueger et al. |
| 5,507,895 A | 4/1996 | Suekane |
| 5,509,914 A | 4/1996 | Osborn, III |
| 5,509,915 A | 4/1996 | Hanson et al. |
| 5,527,300 A | 6/1996 | Sauer |
| 5,527,302 A | 6/1996 | Endres et al. |
| 5,527,304 A | 6/1996 | Buell et al. |
| 5,527,305 A | 6/1996 | Goulait et al. |
| 5,537,722 A | 7/1996 | Neiderhofer et al. |
| 5,540,796 A | 7/1996 | Fries |
| 5,549,591 A | 8/1996 | Landvogt |
| 5,549,592 A | 8/1996 | Fries et al. |
| 5,554,243 A | 9/1996 | Igaue et al. |
| 5,556,394 A | 9/1996 | Roe et al. |
| 5,562,646 A | 10/1996 | Goldman et al. |
| 5,562,650 A | 10/1996 | Everett et al. |
| 5,571,096 A | 11/1996 | Dobrin et al. |
| 5,575,782 A | 11/1996 | Hasse et al. |
| 5,591,151 A | 1/1997 | Hasse et al. |
| 5,593,399 A | 1/1997 | Tanzer et al. |
| 5,595,567 A | 1/1997 | King et al. |
| 5,595,618 A | 1/1997 | Fries et al. |
| 5,599,335 A | 2/1997 | Goldman et al. |
| 5,599,620 A | 2/1997 | Huskey |
| 5,601,542 A | 2/1997 | Melius et al. |
| 5,603,707 A | 2/1997 | Trombetta et al. |
| 5,605,735 A | 2/1997 | Zehner et al. |
| 5,624,423 A | 4/1997 | Anjur et al. |
| 5,624,428 A | 4/1997 | Sauer |
| 5,624,429 A | 4/1997 | Long et al. |
| 5,628,741 A | 5/1997 | Buell et al. |
| 5,629,063 A | 5/1997 | Gobran |
| 5,634,917 A | 6/1997 | Fujioka et al. |
| 5,647,864 A | 7/1997 | Allen et al. |
| 5,659,538 A | 8/1997 | Stuebe et al. |
| 5,660,666 A | 8/1997 | Dilnik et al. |
| 5,669,894 A | 9/1997 | Goldman et al. |
| 5,669,900 A | 9/1997 | Bullwinkel et al. |
| 5,674,216 A | 10/1997 | Buell et al. |
| 5,681,300 A | 10/1997 | Ahr et al. |
| 5,683,533 A | 11/1997 | Keighley et al. |
| 5,683,794 A | 11/1997 | Wadsworth et al. |
| 5,685,873 A | 11/1997 | Bruemmer et al. |
| 5,690,628 A | 11/1997 | Huskey et al. |
| 5,702,377 A | 12/1997 | Collier, IV et al. |
| 5,706,524 A | 1/1998 | Herrin et al. |
| 5,718,698 A | 2/1998 | Dobrin et al. |
| 5,722,127 A | 3/1998 | Coates |
| 5,735,839 A | 4/1998 | Kawaguchi et al. |
| 5,738,669 A | 4/1998 | Suzuki et al. |
| 5,741,241 A | 4/1998 | Guidotti et al. |
| 5,745,922 A | 5/1998 | Rajala et al. |
| 5,746,731 A | 5/1998 | Hisada |
| 5,749,865 A | 5/1998 | Yamamoto et al. |
| 5,749,866 A | 5/1998 | Roe et al. |
| 5,760,080 A | 6/1998 | Wada et al. |
| 5,769,838 A | 6/1998 | Buell et al. |
| 5,772,649 A | 6/1998 | Siudzinski |
| 5,735,840 A | 7/1998 | Kline et al. |
| 5,779,831 A | 7/1998 | Schmitz |
| 5,785,699 A | 7/1998 | Schmitz |
| 5,795,350 A | 8/1998 | Schmitz |
| 5,797,893 A | 8/1998 | Wada et al. |
| 5,817,400 A | 10/1998 | Chen et al. |
| 5,820,617 A | 10/1998 | Igaue et al. |
| 5,830,206 A | 11/1998 | Larsson |
| 5,843,056 A | 12/1998 | Good et al. |
| 5,843,066 A | 12/1998 | Dobrin |
| 5,843,067 A | 12/1998 | Trombetta et al. |
| 5,843,575 A | 12/1998 | Wang et al. |
| 5,849,000 A | 12/1998 | Anjur et al. |
| 5,853,402 A | 12/1998 | Faulks et al. |
| 5,855,574 A | 1/1999 | Kling et al. |
| 5,858,515 A | 1/1999 | Stokes et al. |
| 5,858,535 A | 1/1999 | Wang et al. |
| 5,860,964 A | 1/1999 | Willekens et al. |
| 5,861,074 A | 1/1999 | Wu |
| 5,865,823 A | 2/1999 | Curro |
| 5,876,392 A | 3/1999 | Hisada |
| 5,876,531 A | 3/1999 | Jacobs et al. |
| 5,895,379 A | 4/1999 | Litchholt et al. |
| 5,897,545 A | 4/1999 | Kline et al. |
| 5,897,546 A | 4/1999 | Kido et al. |
| 5,902,296 A | 5/1999 | Fluyeras |
| 5,906,604 A | 5/1999 | Ronnberg et al. |
| 5,916,206 A | 6/1999 | Otsubo et al. |
| 5,919,178 A | 7/1999 | Widlund |
| 5,926,926 A | 7/1999 | Kato |
| 5,928,212 A | 7/1999 | Kline et al. |
| 5,940,887 A | 8/1999 | Rajala et al. |
| 5,941,865 A | 8/1999 | Otsubo et al. |
| 5,948,507 A | 9/1999 | Chen et al. |
| 5,957,906 A | 9/1999 | Roe et al. |
| 5,961,506 A | 10/1999 | Guidotti et al. |
| 5,961,761 A | 10/1999 | Heindel et al. |
| 5,971,970 A | 10/1999 | Carlbark et al. |
| 5,977,430 A | 11/1999 | Roe et al. |
| 5,984,911 A | 11/1999 | Siebers et al. |
| 6,007,527 A | 12/1999 | Kawaguchi et al. |
| 6,011,196 A | 1/2000 | Wang et al. |
| 6,017,621 A | 1/2000 | Hilston et al. |
| 6,020,535 A | 2/2000 | Blenke et al. |
| 6,030,373 A | 2/2000 | Van Gompel et al. |
| 6,036,805 A | 3/2000 | McNichols |
| 6,045,543 A | 4/2000 | Pozniak et al. |
| 6,049,915 A | 4/2000 | Malowaniec |
| 6,049,916 A | 4/2000 | Rajala et al. |
| 6,051,094 A | 4/2000 | Melbye et al. |
| 6,063,067 A | 5/2000 | Takizawa et al. |
| 6,068,620 A | 5/2000 | Chmielewski |
| 6,075,178 A | 6/2000 | Wilhelm et al. |
| 6,077,379 A | 6/2000 | Herrin et al. |
| 6,080,909 A | 6/2000 | Osterdahl et al. |
| 6,083,212 A | 7/2000 | Kumasaka |
| 6,098,203 A | 8/2000 | Rajala et al. |
| 6,107,538 A | 8/2000 | Young et al. |
| 6,107,539 A | 8/2000 | Palumbo et al. |
| 6,117,121 A | 9/2000 | Faulks et al. |
| 6,132,411 A | 10/2000 | Huber et al. |
| 6,140,551 A | 10/2000 | Niemeyer et al. |
| 6,142,986 A | 11/2000 | Lord et al. |
| 6,156,024 A | 12/2000 | Schulte et al. |
| 6,159,584 A | 12/2000 | Eaton et al. |
| 6,179,820 B1 | 1/2001 | Fernfors |
| 6,183,587 B1 | 2/2001 | McFall et al. |
| 6,191,055 B1 | 2/2001 | Boyer, III et al. |
| 6,197,012 B1 | 3/2001 | Mishima et al. |
| 6,198,018 B1 | 3/2001 | Curro |
| 6,213,991 B1 | 4/2001 | Kling et al. |
| 6,213,992 B1 | 4/2001 | Dreier |
| 6,218,593 B1 | 4/2001 | Torimae et al. |
| 6,222,091 B1 | 4/2001 | Beihoffer et al. |
| 6,224,961 B1 | 5/2001 | Hsueh et al. |
| 6,235,011 B1 | 5/2001 | O'Connell |
| 6,240,569 B1 | 6/2001 | Van Gompel et al. |
| 6,241,713 B1 | 6/2001 | Gross et al. |

(56) References Cited

U.S. PATENT DOCUMENTS

| | | |
|---|---|---|
| 6,255,236 B1 | 7/2001 | Cree et al. |
| 6,258,077 B1 | 7/2001 | Buell et al. |
| 6,260,211 B1 | 7/2001 | Rajala et al. |
| 6,264,643 B1 | 7/2001 | Toyoda |
| 6,287,286 B1 | 9/2001 | Akin et al. |
| 6,287,287 B1 | 9/2001 | Elsberg |
| 6,307,119 B1 | 10/2001 | Cammarota et al. |
| 6,307,120 B1 | 10/2001 | Glaug |
| 6,312,420 B1 | 11/2001 | Sasaki et al. |
| 6,315,765 B1 | 11/2001 | Datta et al. |
| 6,316,688 B1 | 11/2001 | Hammons et al. |
| 6,328,725 B2 | 12/2001 | Fernfors |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,368,312 B1 | 4/2002 | Otsubo |
| 6,369,292 B1 | 4/2002 | Strack et al. |
| 6,371,951 B1 | 4/2002 | Koczab et al. |
| 6,375,646 B1 | 4/2002 | Widlund et al. |
| 6,383,960 B1 | 5/2002 | Everett et al. |
| 6,392,116 B1 | 5/2002 | Beihoffer et al. |
| 6,394,991 B1 | 5/2002 | Takei et al. |
| 6,395,115 B1 | 5/2002 | Popp et al. |
| 6,402,730 B1 | 6/2002 | Malowaniec |
| 6,409,858 B1 | 6/2002 | Popp et al. |
| 6,413,249 B1 | 7/2002 | Turi et al. |
| 6,414,216 B1 | 7/2002 | Malowaniec |
| 6,423,046 B1 | 7/2002 | Fujioka et al. |
| 6,428,525 B1 | 8/2002 | Malowaniec |
| 6,428,526 B1 | 8/2002 | Heindel et al. |
| 6,429,352 B1 | 8/2002 | Herrlein et al. |
| 6,432,243 B1 | 8/2002 | Popp et al. |
| 6,432,248 B1 | 8/2002 | Popp et al. |
| 6,437,213 B1 | 8/2002 | Schmidt et al. |
| 6,437,214 B1 | 8/2002 | Everett et al. |
| 6,440,117 B1 | 8/2002 | Itoh et al. |
| 6,447,497 B1 | 9/2002 | Olson |
| 6,447,628 B1 | 9/2002 | Couillard et al. |
| 6,454,751 B1 | 9/2002 | Olson |
| 6,455,753 B1 | 9/2002 | Glaug et al. |
| 6,458,115 B1 | 10/2002 | Lindqvist et al. |
| 6,461,343 B1 | 10/2002 | Schaefer et al. |
| 6,461,344 B1 | 10/2002 | Widlund et al. |
| 6,463,633 B1 | 10/2002 | Sangani et al. |
| 6,463,663 B1 | 10/2002 | Kanzawa |
| 6,465,379 B1 | 10/2002 | Cook et al. |
| D465,842 S | 11/2002 | Magee et al. |
| 6,475,199 B1 | 11/2002 | Gann et al. |
| 6,476,289 B1 | 11/2002 | Buell et al. |
| 6,478,786 B1 | 11/2002 | Glaug et al. |
| 6,481,362 B2 | 11/2002 | Hietpas et al. |
| 6,494,873 B2 | 12/2002 | Karlsson et al. |
| 6,497,032 B2 | 12/2002 | Maxton et al. |
| 6,498,283 B1 | 12/2002 | Wada et al. |
| 6,500,163 B2 | 12/2002 | Rönnberg et al. |
| 6,506,394 B1 | 1/2003 | Yahiaoui et al. |
| 6,506,959 B2 | 1/2003 | Hamajima et al. |
| 6,509,513 B2 | 1/2003 | Glaug et al. |
| 6,513,221 B2 | 2/2003 | Vogt et al. |
| 6,514,187 B2 | 2/2003 | Coenen et al. |
| 6,524,294 B1 | 2/2003 | Hilston et al. |
| 6,533,879 B2 | 3/2003 | Quereshi et al. |
| 6,540,731 B2 | 4/2003 | Magnussson et al. |
| 6,544,244 B1 | 4/2003 | Glaug et al. |
| 6,551,295 B1 | 4/2003 | Schmidt et al. |
| 6,566,578 B1 | 5/2003 | Glaug et al. |
| 6,569,139 B1 | 5/2003 | Datta et al. |
| 6,570,058 B1 | 5/2003 | Fuchs et al. |
| 6,572,595 B1 | 6/2003 | Klemp et al. |
| 6,575,949 B1 | 6/2003 | Waksmundzki et al. |
| 6,575,952 B2 | 6/2003 | Kirk et al. |
| 6,579,275 B1 | 6/2003 | Pozniak et al. |
| 6,582,543 B1 | 6/2003 | Nilsson et al. |
| 6,590,136 B1 | 7/2003 | Young et al. |
| 6,595,976 B2 | 7/2003 | Shimoe et al. |
| 6,596,113 B2 | 7/2003 | Csida et al. |
| 6,602,238 B2 | 8/2003 | Takei et al. |
| 6,610,904 B1 | 8/2003 | Thomas et al. |
| 6,623,576 B2 | 9/2003 | Mitchell et al. |
| 6,626,881 B2 | 9/2003 | Shingu et al. |
| 6,626,882 B2 | 9/2003 | Hjorth |
| 6,630,611 B1 | 10/2003 | Malowaniec |
| 6,632,209 B1 | 10/2003 | Chmielewski |
| 6,635,041 B1 | 10/2003 | Popp et al. |
| 6,635,135 B2 | 10/2003 | Kuen et al. |
| 6,642,431 B1 | 11/2003 | Gellerstedt et al. |
| 6,645,338 B1 | 11/2003 | Sangani et al. |
| 6,646,179 B1 | 11/2003 | Melius et al. |
| 6,646,180 B1 | 11/2003 | Chmielewski |
| 6,648,870 B2 | 11/2003 | Itoh et al. |
| 6,648,871 B2 | 11/2003 | Kusibojoska et al. |
| 6,649,810 B1 | 11/2003 | Minato et al. |
| 6,664,439 B1 | 12/2003 | Arndt et al. |
| 6,669,678 B2 | 12/2003 | Hermansson et al. |
| 6,673,984 B1 | 1/2004 | Roe et al. |
| 6,676,645 B1 | 1/2004 | Bitterhof |
| 6,689,934 B2 | 2/2004 | Dodge, II et al. |
| 6,692,477 B2 | 2/2004 | Gibbs |
| 6,700,036 B2 | 3/2004 | Thomas et al. |
| 6,702,798 B2 | 3/2004 | Christoffel et al. |
| 6,709,423 B1 | 3/2004 | Herrlein et al. |
| 6,710,225 B1 | 3/2004 | Everett et al. |
| 6,719,744 B2 | 4/2004 | Kinnear et al. |
| 6,723,035 B2 | 4/2004 | Franklin et al. |
| 6,723,892 B1 | 4/2004 | Daley et al. |
| 6,726,669 B2 | 4/2004 | Shimada et al. |
| 6,726,670 B2 | 4/2004 | Almberg et al. |
| 6,727,403 B1 | 4/2004 | Ehrnsperger et al. |
| 6,733,483 B2 | 5/2004 | Raufman et al. |
| 6,736,804 B1 | 5/2004 | Robertson et al. |
| 6,740,071 B2 | 5/2004 | Gibbs |
| 6,749,860 B2 | 6/2004 | Tyrrell et al. |
| 6,755,808 B2 | 6/2004 | Balogh et al. |
| 6,761,711 B1 | 7/2004 | Fletcher et al. |
| 6,764,479 B2 | 7/2004 | Kusibojoska et al. |
| 6,770,065 B1 | 8/2004 | Sasaki et al. |
| 6,776,316 B2 | 8/2004 | Van Eperen et al. |
| 6,780,173 B2 | 8/2004 | Mishima et al. |
| 6,780,272 B2 | 8/2004 | Wood |
| 6,790,798 B1 | 9/2004 | Suzuki et al. |
| 6,803,496 B2 | 10/2004 | Elder et al. |
| 6,838,591 B2 | 1/2005 | Waksmundzki et al. |
| 6,840,928 B2 | 1/2005 | Datta et al. |
| 6,846,374 B2 | 1/2005 | Popp et al. |
| 6,849,067 B2 | 2/2005 | Fletcher et al. |
| 6,878,223 B2 | 4/2005 | Kuen et al. |
| 6,878,647 B1 | 4/2005 | Rezai et al. |
| 6,885,451 B2 | 4/2005 | Vogt et al. |
| 6,888,043 B2 | 5/2005 | Geiser et al. |
| 6,888,044 B2 | 5/2005 | Fell et al. |
| 6,888,143 B2 | 5/2005 | Vogt et al. |
| 6,891,080 B2 | 5/2005 | Minato et al. |
| 6,904,865 B2 | 6/2005 | Klofta et al. |
| 6,911,024 B2 | 6/2005 | Kusibojoska et al. |
| 6,923,798 B2 | 8/2005 | Hedén et al. |
| 6,936,129 B2 | 8/2005 | Karami et al. |
| 6,945,968 B2 | 9/2005 | Svensson et al. |
| 6,946,585 B2 | 9/2005 | Brown |
| 6,953,452 B2 | 10/2005 | Popp et al. |
| 6,955,668 B2 | 10/2005 | Almberg et al. |
| 6,969,553 B1 | 11/2005 | Tam et al. |
| 6,972,011 B2 | 12/2005 | Maeda et al. |
| 6,972,012 B1 | 12/2005 | Pozniak et al. |
| 6,981,968 B2 | 1/2006 | Kusibojoska et al. |
| 6,991,622 B2 | 1/2006 | Nakaoka et al. |
| 6,994,761 B2 | 2/2006 | Klemp |
| 7,000,260 B2 | 2/2006 | Rajala et al. |
| 7,001,368 B2 | 2/2006 | Otsubo |
| 7,018,369 B2 | 3/2006 | Vangompel et al. |
| 7,044,133 B2 | 5/2006 | Lohrengel et al. |
| 7,048,725 B2 | 5/2006 | Kling et al. |
| 7,060,058 B2 | 6/2006 | Otsubo et al. |
| D527,102 S | 8/2006 | Mills et al. |
| 7,087,046 B2 | 8/2006 | Van Gompel et al. |

(56) References Cited

U.S. PATENT DOCUMENTS

| | | |
|---|---|---|
| 7,090,667 B2 | 8/2006 | Fell et al. |
| D527,818 S | 9/2006 | Mills et al. |
| 7,156,939 B2 | 1/2007 | Vogt et al. |
| 7,163,745 B2 | 1/2007 | Mangold et al. |
| 7,166,094 B2 | 1/2007 | Glaug et al. |
| 7,172,585 B2 | 2/2007 | Sandin et al. |
| 7,175,910 B2 | 2/2007 | Ehrnsperger et al. |
| 7,195,622 B2 | 3/2007 | Lindström |
| 7,201,743 B2 | 4/2007 | Röhrl |
| 7,204,907 B2 | 4/2007 | Cree et al. |
| 7,217,261 B2 | 5/2007 | Otsubo et al. |
| 7,270,881 B2 | 9/2007 | Schmidt et al. |
| 7,285,178 B2 | 10/2007 | Mischler et al. |
| 7,314,465 B2 | 1/2008 | Van Gompel et al. |
| 7,322,967 B2 | 1/2008 | Kondo |
| 7,331,946 B2 | 2/2008 | Shimada et al. |
| 7,332,642 B2 | 2/2008 | Liu |
| 7,344,525 B2 | 3/2008 | Linker, III et al. |
| 7,347,846 B2 | 3/2008 | Hermansson et al. |
| 7,368,027 B2 | 5/2008 | Schneider et al. |
| 7,373,698 B2 | 5/2008 | Erdman et al. |
| 7,378,567 B2 | 5/2008 | Mangold |
| 7,378,568 B2 | 5/2008 | Thomas et al. |
| 7,387,148 B2 | 6/2008 | Vogt et al. |
| 7,396,349 B2 | 7/2008 | Van Himbergen et al. |
| 7,396,585 B2 | 7/2008 | Schmidt et al. |
| 7,402,339 B2 | 7/2008 | Schmidt et al. |
| 7,411,110 B2 | 8/2008 | Sawyer et al. |
| 7,425,242 B2 | 9/2008 | Olsson et al. |
| 7,432,413 B2 | 10/2008 | Roe et al. |
| 7,435,245 B2 | 10/2008 | Wendelstorf et al. |
| 7,438,709 B2 | 10/2008 | Karami et al. |
| 7,449,014 B2 | 11/2008 | Oba et al. |
| 7,455,665 B2 | 11/2008 | Wendelstorf et al. |
| 7,462,754 B2 | 12/2008 | Malowaniec |
| 7,462,756 B2 | 12/2008 | Malowaniec |
| 7,482,505 B2 | 1/2009 | Stupperich et al. |
| 7,488,535 B2 | 2/2009 | Ehrnsperger et al. |
| 7,524,313 B2 | 4/2009 | Kline et al. |
| 7,524,449 B2 | 4/2009 | Walsh et al. |
| 7,524,561 B2 | 4/2009 | Schmidt et al. |
| 7,527,618 B2 | 5/2009 | Benning et al. |
| 7,534,481 B2 | 5/2009 | Seth et al. |
| 7,544,628 B2 | 6/2009 | Stupperich et al. |
| 7,559,124 B2 | 7/2009 | Poulakis |
| 7,569,039 B2 | 8/2009 | Matsuda et al. |
| 7,569,041 B2 | 8/2009 | Stupperich et al. |
| 7,604,624 B2 | 10/2009 | Veith et al. |
| 7,621,901 B2 | 11/2009 | Karami |
| 7,682,349 B2 | 3/2010 | Popp et al. |
| 7,687,680 B2 | 3/2010 | Fell et al. |
| 7,695,464 B2 | 4/2010 | Fletcher et al. |
| 7,699,825 B2 | 4/2010 | Nakagawa et al. |
| 7,713,371 B2 | 5/2010 | Lohrengel et al. |
| 7,718,021 B2 | 5/2010 | Venturino et al. |
| 7,722,590 B2 | 5/2010 | Tsuji et al. |
| 7,737,324 B2 | 6/2010 | Lavon et al. |
| 7,744,576 B2 | 6/2010 | Busam et al. |
| 7,744,713 B2 | 6/2010 | Blessing et al. |
| 7,749,211 B2 | 7/2010 | Van Gompel et al. |
| 7,750,203 B2 | 7/2010 | Becker et al. |
| 7,758,558 B2 | 7/2010 | Otsubo |
| D624,696 S | 9/2010 | Hsiao |
| 7,794,442 B2 | 9/2010 | Roehrl et al. |
| 7,794,839 B2 | 9/2010 | Schmidt et al. |
| 7,807,861 B2 | 10/2010 | Molander et al. |
| 7,819,851 B2 | 10/2010 | Karlsson |
| 7,837,662 B2 | 11/2010 | Nakagawa et al. |
| 7,838,721 B2 | 11/2010 | Chen |
| 7,838,722 B2 | 11/2010 | Blessing et al. |
| 7,851,667 B2 | 12/2010 | Becker et al. |
| 7,851,669 B2 | 12/2010 | Nakagawa et al. |
| 7,857,801 B2 | 12/2010 | Hamall et al. |
| 7,863,498 B2 | 1/2011 | Roe et al. |
| 7,867,213 B2 | 1/2011 | Bandorf et al. |
| 7,906,065 B1 | 3/2011 | Brown et al. |
| 7,918,959 B2 | 4/2011 | Hornung et al. |
| 7,923,597 B2 | 4/2011 | Ponomarenko et al. |
| 7,935,299 B2 | 5/2011 | Walsh et al. |
| 7,943,537 B2 | 5/2011 | Vincent et al. |
| 7,947,865 B2 | 5/2011 | Fossum et al. |
| 7,956,236 B2 | 6/2011 | Ponomarenko et al. |
| 7,993,320 B2 | 8/2011 | Hornung et al. |
| 7,994,384 B2 | 8/2011 | Qin et al. |
| 8,016,806 B2 | 9/2011 | Hornung et al. |
| 8,017,827 B2 | 9/2011 | Hundorf et al. |
| 8,025,652 B2 | 9/2011 | Hornung et al. |
| 8,038,662 B2 | 10/2011 | Hornung et al. |
| 8,083,724 B2 | 12/2011 | Bittner et al. |
| 8,088,967 B2 | 1/2012 | Underhill et al. |
| 8,100,173 B2 | 1/2012 | Hornung et al. |
| 8,138,388 B2 | 3/2012 | Elder et al. |
| 8,142,590 B2 | 3/2012 | Rajala et al. |
| 8,148,598 B2 | 4/2012 | Tsang et al. |
| 8,152,788 B2 | 4/2012 | Beckert et al. |
| 8,158,848 B2 | 4/2012 | Swerev et al. |
| 8,162,913 B2 | 4/2012 | Goates et al. |
| 8,180,603 B2 | 5/2012 | Blessing et al. |
| 8,187,240 B2 | 5/2012 | Busam et al. |
| 8,202,390 B2 | 6/2012 | Malowaniec |
| 8,206,533 B2 | 6/2012 | Hundorf et al. |
| 8,221,372 B2 | 7/2012 | Kouno et al. |
| 8,221,379 B2 | 7/2012 | Lam et al. |
| 8,221,672 B2 | 7/2012 | Brown et al. |
| 8,231,593 B2 | 7/2012 | Nakagawa et al. |
| 8,251,967 B2 | 8/2012 | Malowaniec |
| 8,258,366 B2 | 9/2012 | Wendelstorf |
| 8,263,820 B2 | 9/2012 | Carlucci et al. |
| 8,282,617 B2 | 10/2012 | Kaneda |
| 8,303,562 B2 | 11/2012 | Hornung et al. |
| 8,319,005 B2 | 11/2012 | Becker et al. |
| 8,343,296 B2 | 1/2013 | Blessing et al. |
| 8,353,891 B2 | 1/2013 | Hornung et al. |
| 8,430,857 B2 | 4/2013 | Labit et al. |
| 8,454,572 B2 | 6/2013 | Roe et al. |
| 8,454,782 B2 | 6/2013 | Ostertag |
| 8,466,336 B2 | 6/2013 | Carlucci et al. |
| 8,476,173 B2 | 7/2013 | Dovertie et al. |
| 8,496,637 B2 | 7/2013 | Hundorf et al. |
| 8,512,305 B2 | 8/2013 | Dziezok et al. |
| 8,518,539 B2 | 8/2013 | Meyer et al. |
| 8,552,252 B2 | 10/2013 | Hundorf et al. |
| 8,585,666 B2 | 11/2013 | Weisman et al. |
| 8,616,867 B2 | 12/2013 | Brown et al. |
| 8,622,984 B2 | 1/2014 | Rajala et al. |
| 8,663,186 B2 | 3/2014 | Lam et al. |
| 8,668,975 B2 | 3/2014 | Westwood |
| 8,672,915 B2 | 3/2014 | Kuwano et al. |
| 8,708,990 B2 | 4/2014 | Beckert et al. |
| 8,747,379 B2 | 6/2014 | Fletcher et al. |
| 8,771,249 B2 | 7/2014 | Beckert et al. |
| 8,784,398 B2 | 7/2014 | Beckert et al. |
| 8,864,733 B2 | 10/2014 | Koenig et al. |
| D716,938 S | 11/2014 | Fitter et al. |
| 8,920,399 B2 | 12/2014 | Mills |
| 9,439,811 B2 | 9/2016 | Love et al. |
| D768,963 S | 10/2016 | Amrikhas et al. |
| 9,486,368 B2 | 11/2016 | Nelson |
| 2001/0023341 A1 | 9/2001 | Karami |
| 2001/0034512 A1 | 10/2001 | Karlsson et al. |
| 2001/0042584 A1 | 11/2001 | Karami et al. |
| 2002/0045881 A1 | 4/2002 | Kusibojoska et al. |
| 2002/0111596 A1 | 8/2002 | Fletcher et al. |
| 2002/0115969 A1 | 8/2002 | Maeda et al. |
| 2002/0123733 A1 | 9/2002 | Itch et al. |
| 2002/0138056 A1 | 9/2002 | Kuen et al. |
| 2002/0138062 A1 | 9/2002 | Kuen et al. |
| 2002/0148548 A1 | 10/2002 | Murie et al. |
| 2002/0156441 A1 | 10/2002 | Sawyer et al. |
| 2002/0177829 A1 | 11/2002 | Fell et al. |
| 2003/0022581 A1 | 1/2003 | Tsai et al. |
| 2003/0023225 A1 | 1/2003 | Sayama |
| 2003/0055394 A1 | 3/2003 | Gibbs |
| 2003/0097113 A1 | 5/2003 | Molee |

(56) References Cited

U.S. PATENT DOCUMENTS

| | | |
|---|---|---|
| 2003/0100878 A1 | 5/2003 | Leak et al. |
| 2003/0105446 A1 | 6/2003 | Hutson et al. |
| 2003/0113507 A1 | 6/2003 | Niemeyer et al. |
| 2003/0114808 A1* | 6/2003 | Underhill ............... A61F 13/84 604/361 |
| 2003/0119404 A1 | 6/2003 | Belau et al. |
| 2003/0199843 A1 | 10/2003 | Kato et al. |
| 2004/0044324 A1 | 3/2004 | Swenson et al. |
| 2004/0102755 A1 | 5/2004 | Morman et al. |
| 2004/0122410 A1 | 6/2004 | Itch et al. |
| 2004/0133180 A1 | 7/2004 | Mori et al. |
| 2004/0158212 A1 | 8/2004 | Ponomarenko et al. |
| 2004/0243086 A1 | 12/2004 | Van Gompel et al. |
| 2005/0020992 A1 | 1/2005 | Van Gompel |
| 2005/0027279 A1 | 2/2005 | Minato et al. |
| 2005/0075618 A1 | 4/2005 | Kenmochi et al. |
| 2005/0143709 A1 | 6/2005 | Lindstrom |
| 2005/0148960 A1 | 7/2005 | Price |
| 2005/0175269 A1 | 8/2005 | Ashton et al. |
| 2005/0256494 A1 | 11/2005 | Datta |
| 2005/0256496 A1 | 11/2005 | Benning et al. |
| 2005/0273067 A1 | 12/2005 | Malowaniec et al. |
| 2006/0024433 A1 | 2/2006 | Blessing et al. |
| 2006/0025733 A1 | 2/2006 | Kikuchi et al. |
| 2006/0036230 A1 | 2/2006 | Mills et al. |
| 2006/0058772 A1 | 3/2006 | Karami |
| 2006/0069370 A1 | 3/2006 | Ellingson et al. |
| 2006/0069379 A1 | 3/2006 | Van Gompel et al. |
| 2006/0121811 A1 | 6/2006 | Mangold et al. |
| 2006/0135923 A1 | 6/2006 | Boggs et al. |
| 2006/0135928 A1 | 6/2006 | Karlsson et al. |
| 2006/0135932 A1 | 6/2006 | Abuto et al. |
| 2006/0155254 A1 | 7/2006 | Sanz et al. |
| 2006/0167424 A1 | 7/2006 | Chang et al. |
| 2006/0184149 A1 | 8/2006 | Kasai et al. |
| 2006/0195068 A1 | 8/2006 | Lawando |
| 2006/0241560 A1 | 10/2006 | Chang et al. |
| 2006/0247596 A1 | 11/2006 | Van Dyke |
| 2006/0258250 A1 | 11/2006 | Mangold et al. |
| 2006/0276765 A1 | 12/2006 | Swerev et al. |
| 2006/0282053 A1 | 12/2006 | Rohrl |
| 2007/0000987 A1 | 1/2007 | Karlsson |
| 2007/0016155 A1 | 1/2007 | Chang et al. |
| 2007/0016158 A1 | 1/2007 | Endres et al. |
| 2007/0038199 A1 | 2/2007 | Erdman et al. |
| 2007/0044903 A1 | 3/2007 | Wisneski et al. |
| 2007/0048497 A1 | 3/2007 | Zhou et al. |
| 2007/0049892 A1 | 3/2007 | Lord et al. |
| 2007/0066950 A1 | 3/2007 | Nelson |
| 2007/0073260 A1 | 3/2007 | Roe |
| 2007/0073262 A1 | 3/2007 | Babusik et al. |
| 2007/0208317 A1 | 9/2007 | Krautkramer et al. |
| 2007/0239131 A1 | 10/2007 | Hermansson et al. |
| 2007/0255246 A1 | 11/2007 | Schneider |
| 2007/0293833 A1 | 12/2007 | Wennerback |
| 2007/0293835 A1 | 12/2007 | Roehrl et al. |
| 2008/0026178 A1 | 1/2008 | Stupperich et al. |
| 2008/0051747 A1 | 2/2008 | Cohen |
| 2008/0103414 A1 | 5/2008 | Song |
| 2008/0108964 A1 | 5/2008 | Edwall |
| 2008/0125735 A1 | 5/2008 | Busam et al. |
| 2008/0134487 A1 | 6/2008 | Hartono |
| 2008/0161767 A1 | 7/2008 | Sandin et al. |
| 2008/0208152 A1 | 8/2008 | Eckstein et al. |
| 2008/0249493 A1 | 10/2008 | Kobayashi et al. |
| 2008/0281286 A1 | 11/2008 | Petersen |
| 2008/0286320 A1 | 11/2008 | Vega et al. |
| 2008/0287897 A1 | 11/2008 | Guzman Reyes et al. |
| 2008/0287898 A1 | 11/2008 | Guzman Reyes et al. |
| 2008/0287899 A1 | 11/2008 | Morrell-Schwartz et al. |
| 2008/0312618 A1 | 12/2008 | Hundorf et al. |
| 2008/0312628 A1 | 12/2008 | Hundorf et al. |
| 2008/0312631 A1 | 12/2008 | Okuda |
| 2009/0084497 A1 | 4/2009 | Hornung et al. |
| 2009/0177176 A1 | 7/2009 | Saito |
| 2009/0198205 A1 | 8/2009 | Malowaniec et al. |
| 2009/0264851 A1* | 10/2009 | Richlen ............... A61F 13/5519 604/385.28 |
| 2009/0275911 A1 | 11/2009 | Hormung et al. |
| 2009/0312736 A1 | 12/2009 | Schroer, Jr. et al. |
| 2009/0326499 A1 | 12/2009 | Veith |
| 2009/0326503 A1 | 12/2009 | Lakso et al. |
| 2010/0051170 A1 | 3/2010 | Nakakado |
| 2010/0063468 A1 | 3/2010 | Lehto et al. |
| 2010/0065199 A1 | 3/2010 | Hormung et al. |
| 2010/0076390 A1 | 3/2010 | Norby et al. |
| 2010/0108251 A1 | 5/2010 | Malowaniec |
| 2010/0163161 A1 | 7/2010 | Gann |
| 2010/0168705 A1 | 7/2010 | Stabelfeldt et al. |
| 2010/0198178 A1 | 8/2010 | Litvay |
| 2010/0285286 A1 | 11/2010 | Middlesworth |
| 2010/0292663 A1 | 11/2010 | Lavon et al. |
| 2010/0318055 A1 | 12/2010 | Hornung et al. |
| 2011/0071488 A1 | 3/2011 | Kuwno et al. |
| 2011/0098668 A1 | 4/2011 | Thorson et al. |
| 2011/0123775 A1 | 5/2011 | Westwood |
| 2011/0130275 A1 | 6/2011 | Weismantel et al. |
| 2011/0144610 A1 | 6/2011 | Karlson et al. |
| 2011/0146892 A1 | 6/2011 | Ostertag |
| 2011/0160692 A1 | 6/2011 | Wilkes et al. |
| 2011/0208140 A1 | 8/2011 | Roe et al. |
| 2011/0208142 A1 | 8/2011 | Roe et al. |
| 2012/0028777 A1 | 2/2012 | Knecht |
| 2012/0053552 A1 | 3/2012 | Van Gompel et al. |
| 2012/0065607 A1 | 3/2012 | Konig et al. |
| 2012/0165777 A1 | 6/2012 | Beckert et al. |
| 2012/0172828 A1 | 7/2012 | Koenig et al. |
| 2012/0310193 A1 | 12/2012 | Ostertag |
| 2013/0144245 A1 | 6/2013 | Roe |
| 2013/0211365 A1 | 8/2013 | Rajala et al. |
| 2013/0261589 A1 | 10/2013 | Fujkawa et al. |
| 2013/0281957 A1 | 10/2013 | Fritz et al. |
| 2013/0345667 A1 | 12/2013 | Nelson et al. |
| 2014/0046286 A1 | 2/2014 | Homann et al. |
| 2015/0011958 A1 | 1/2015 | Yoshioka |
| 2015/0297421 A1 | 10/2015 | Nelson |
| 2015/0297423 A1 | 10/2015 | Nelson |

FOREIGN PATENT DOCUMENTS

| | | |
|---|---|---|
| EP | 1719484 A1 | 11/2006 |
| EP | 1736127 A1 | 12/2006 |
| EP | 1941853 A1 | 7/2008 |
| WO | 199619959 A1 | 7/1996 |
| WO | 1998043574 A1 | 10/1998 |
| WO | 1999023985 A1 | 5/1999 |
| WO | 1999048452 A1 | 9/1999 |
| WO | 2006017718 A1 | 2/2006 |
| WO | 2008002840 A2 | 1/2008 |
| WO | 2012054591 A1 | 4/2012 |
| WO | 2015164170 A1 | 10/2015 |

OTHER PUBLICATIONS

Paul Hartmann AG, Notice of Opposition to European Patent No. 2629730, filed in the European Patent Office Jun. 12, 2019.

Paul Hartmann AG, Citation in Opposition Procedure (Anlage 1.7.4) re European Patent No. 2629730, filed in European Patent Office Jun. 12, 2019.

Paul Hartmann AG, Citation in Opposition Procedure (Anlage 1 7.3) re European Patent No. 2629730, filed in European Patent Office Jun. 6, 2019.

Paul Hartmann AG, Citation in Opposition Procedure (Anlage 1.7.2) re European Patent No. 2629730, filed in European Patent Office Jun. 6, 2019.

Paul Hartmann AG, Citation in Opposition Procedure (Anlage 1.7.1) re European Patent No. 2629730, filed in European Patent Office Jun. 6, 2019.

Paul Hartmann AG, Citation in Opposition Procedure (Anlage 1.7) re European Patent No. 2629730, filed in European Patent Office Jun. 6, 2019.

(56) References Cited

OTHER PUBLICATIONS

Paul Hartmann AG, Citation in Opposition Procedure (Anlage 1.6 Gr. 3) re European Patent No. 2629730, filed in European Patent Office Jun. 6, 2019.
Paul Hartmann AG, Citation in Opposition Procedure (Anlage 1.6 Gr. 2) re European Patent No. 2629730, filed in European Patent Office Jun. 6, 2019.
Paul Hartmann AG, Citation in Opposition Procedure (Anlage 1.5 Gr. 3) re European Patent No. 2629730, filed in European Patent Office Jun. 6, 2019.
Paul Hartmann AG, Citation in Opposition Procedure (Anlage 1.5 Gr. 2) re European Patent No. 2629730, filed in European Patent Office Jun. 6, 2019.
Paul Hartmann AG, Citation in Opposition Procedure (Anlage 1.4) re European Patent No. 2629730, filed in European Patent Office Jun. 6, 2019.
Paul Hartmann AG, Citation in Opposition Procedure (Anlage 1.3 Gr. 3) re European Patent No. 2629730, filed in European Patent Office Jun. 6, 2019.
Paul Hartmann AG, Citation in Opposition Procedure (Anlage 1.3 Gr. 2) re European Patent No. 2629730, filed in European Patent Office Jun. 6, 2019.
Paul Hartmann AG, Citation in Opposition Procedure (Anlage 1.2) re European Patent No. 2629730, filed in European Patent Office Jun. 6, 2019.
Paul Hartmann AG, Citation in Opposition Procedure (Anlage 1.1) re European Patent No. 2629730, filed in European Patent Office Jun. 6, 2019.
Paul Hartmann AG, Citation in Opposition Procedure (Anlage 1.8) re European Patent No. 2629730, filed in European Patent Office Jun. 6, 2019.
Medline Industries, Inc., Reply of the Patent Proprietor to the Notice(s) of Opposition re European Patent No. 2629730, filed in the European Patent Office Oct. 28, 2019.
European Patent Office, Communication, EPO Form 2906, Opposition re European Patent No. 2629730; Jan. 3, 2020.
Medline Industries, Inc., Written Submission in Preparation to/during Oral Proceedings, Opposition re European Patent No. 2629730, Jul. 16, 2020.
Paul Hartmann AG, Written Submission in Preparation to/during Oral Proceedings, Opposition re European Patent No. 2629730, Sep. 14, 2020.
Paul Hartmann AG, Affidavit of Anton Eckle, Annex to Written Submission in Preparation to/during Oral Proceedings, Opposition re European Patent No. 2629730, filed in European Patent Office Sep. 14, 2020 (Aug. 13, 2020).
Paul Hartmann AG, Affidavit of Rudiger Kesselmeier, Annex to Written Submission in Preparation to/during Oral Proceedings, Opposition re European Patent No. 2629730, filed in European Patent Office Sep. 14, 2020 (Aug. 20, 2020).
Medline Industries, Inc., Written Submission in Preparation to/during Oral Proceedings, Opposition re European Patent No. 2629730, Feb. 11, 2021.
European Patent Office, Information, EPO Form 2341, Opposition re European Patent No. 2629730; Apr. 13, 2021.
European Patent Office, Decision Revoking the European Patent, EPO Form 2331, Opposition re European Patent No. 2629730; Aug. 2, 2021.
Medline Industries, Inc., Notice of Appeal, Opposition re European Patent No. 2629730, Nov. 17, 2021.
Medline Industries, Inc., Statement of Grounds of Appeal, Opposition re European Patent No. 2629730, Dec. 13, 2021.

* cited by examiner

ABSORBENT ARTICLES AND METHODS OF MANUFACTURING THE SAME

RELATED APPLICATION

This application is a continuation of copending U.S. patent application Ser. No. 13/832,965 filed Mar. 15, 2013 and entitled "ABSORBENT ARTICLES AND METHODS OF MANUFACTURING THE SAME," which application is a continuation-in-part of U.S. patent application Ser. No. 13/276,843, now U.S. Pat. No. 9,439,811, filed Oct. 19, 2011, which application claims priority to U.S. Provisional Application No. 61/394,758 filed Oct. 19, 2010. The contents of each of these applications are herein incorporated by reference in their entirety.

BACKGROUND

The present invention relates generally to absorbent articles and, in particular, to absorbent articles having improved fit, comfort and manufacturability.

Millions of people of all ages suffer from incontinence of the bowel or bladder. Whether an infant, adult, or elderly person, the underlying cause of incontinence varies but the method of treatment typically involves absorbent article products. Adult incontinent briefs, disposable diapers and underpads can alleviate some of the emotional and physical discomfort of incontinence by absorbing and containing liquid and other discharges from the human body to prevent body and clothing soiling.

Despite recent pressure from Center for Medicaid and Medicare Services (CMS) to change clinical practice to promote systematic treatment of incontinence, improper use of absorbent incontinent products for the management of urinary and fecal incontinence continues. The high prevalence of incontinence in nursing home residents results in Incontinence Associated Dermatitis (IAD) in the perineal area and is a common complication. Improper fit or use, applying the wrong size to a user, of absorbent articles is a contributing factor to perineal dermatitis by creating increase heat build-up or chafing against the superficial skin tissue.

In an attempt to improve performance and reduce abrasion to the skin, the absorbent articles industry has been introducing new product concepts with, for example, nonwoven back sheets for better comfort. However, these products still contribute to the development of IAD due to the improper size and design in the crotch chaises and leg cut out. In an attempt to size the garments appropriately, a majority of current absorbent articles are sold in five sizes: Medium, Regular, Large, Extra Large and 2X Large. These sizes however do not resolve the above issues as the articles do not sufficiently accommodate users with different body size proportions. As a result, caregivers constantly need to use a larger, oversized garment because the product design does not allow for good fit around the patient's waist and thigh leg area at the same time. Thus, caregivers are placing larger garments on the patient to compensate which leads to higher cost; potential leakage; and lower dignity because of a bigger bulky garment being worn.

Further, not using the correct size garment on a patient who suffers from incontinence violates the federal governments CMS-F315 rules that require care professionals and staff to use the correct size and type of garment based on the patient's condition and size.

Additionally, multiple sizes are created by multiple size components leading to inefficient manufacturing process. Each size requires the manufacturer to stop the machine and change out a number of the machine's sections in order to produce the next size. After changing the machine sections, other sections need to be recalibrated in order to insure the raw material components are converted correctly. These changeovers can take anywhere between 6 to 12 hours depending on the machine being used by the manufacturer. This downtime reduces the amount of product the machine can produce and increases the manufacturers converting cost. Further, current adult brief machines manufactures are required to use extra steel and other materials in order to build the additional components for the additional sizes.

In another attempt to improve performance and fit, incontinence articles are configured with stretchable material attached to the back panel of the article's ears. However the stretch briefs have shorter front panels in order to offset the cost of stretch material. First this requires the caregiver to use a different application technique because the attachment zone is smaller. Second, the stretch material, when extended fully to accommodate a larger waist for patients who at the upper limit of sizing, can cause skin irritation and breakdown, particularly in the waist and hip region. Often the waist securement portions are over-stretched and incorrectly fit, traumatizing the skin as it lays adjacent to.

In an attempt to improve the performance of an absorbent layer of the incontinence article, the top of a core of the absorbent layer can be embossed. Embossing the top of the absorbent layer can increase the lateral movement of fluid that comes in contact with the absorbent layer and can reduce leakage, but it can also increase circular movement of the fluid and increase leakage. Similarly, absorbent layers having two cores have similar advantages and disadvantages. In addition, flow between the top core and the bottom core can be insufficient, even when the top of the bottom core is embossed.

In addition, when donning the product, significant forces may be subjected upon the side panels, especially while the product is being applied and the wearer's body weight is directly on the chassis of the absorbent article. These forces can be localized along one edge of the article, and therefore can cause a failure, for example, a tear in the panel, which propagates quickly and completely across the span of the panel, thereby causing a complete failure of the article.

Additionally, a patient with skin care concerns in the hip region may benefit from a product that can provide softness and a more comfortable side panel. Additionally, as adult brief products have evolved, these products now include side panels that are used for closure. As these side panels are used, it is possible for the wearer to don the product in such a way that the side panel can bunch, and cause pressure lines against the wearer. Additionally, when the product is manufactured, the process of applying the side panel to the diaper includes a manufacturing step of folding a portion of the side panel. If elements of the manufacturing process are not ideal, scrap can be created in the manufacturing process.

Accordingly, a need exists for absorbent articles that provide a better fit and comfort, and increased absorption, while reducing the number of sizes within a range of products, reducing manufacturing costs, and reducing the impact on the environment. A need also exists for absorbent articles that will resist bunching, while at the same time providing softness and the effect of padding for the wearer. A further need exists to improve the ability to fold this side panel during the manufacturing process.

BRIEF DESCRIPTION OF THE DRAWINGS

The foregoing and other advantages of the invention will become apparent upon reading the following detailed description and upon reference to the drawings.

Figure 1:
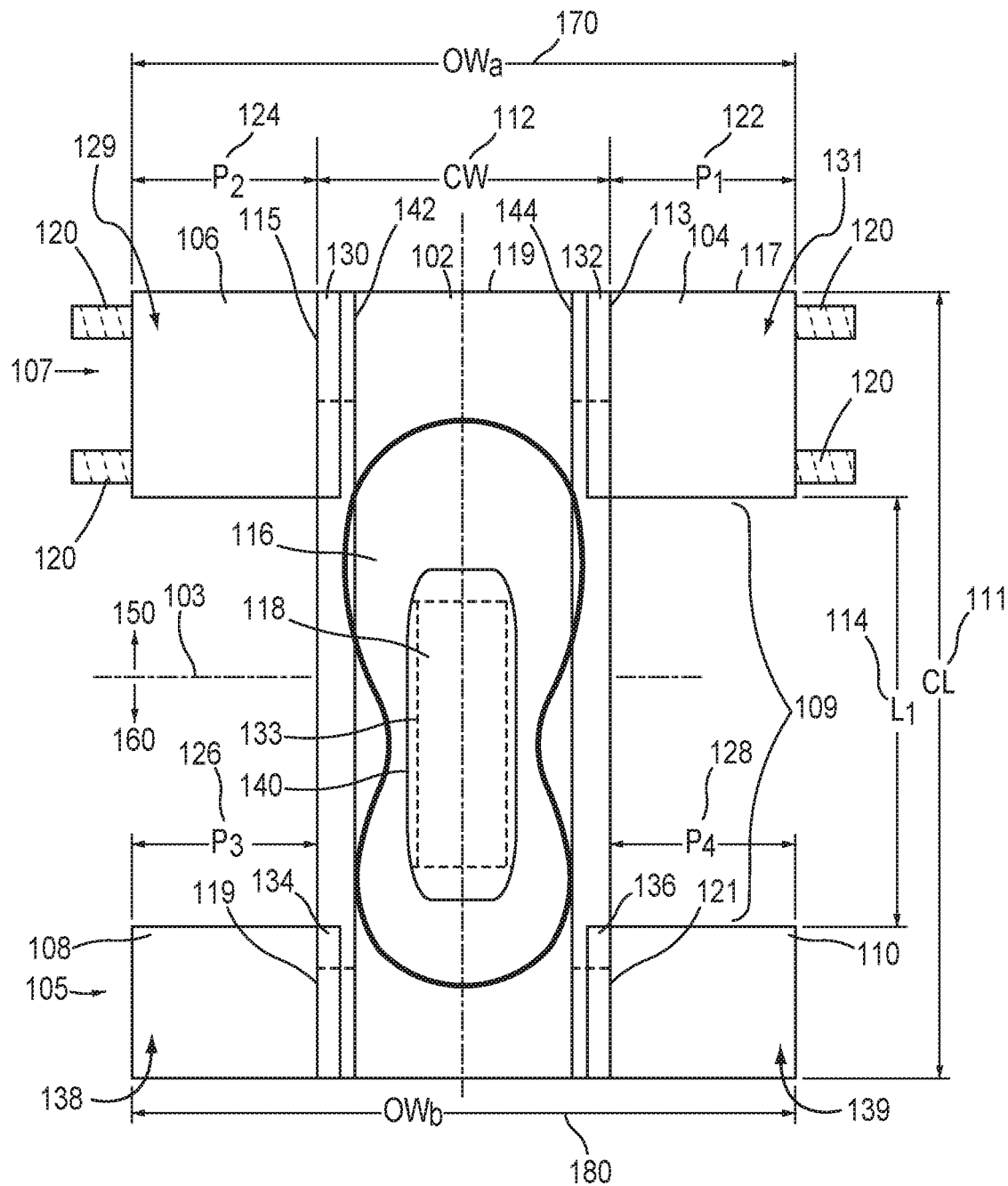
FIG. 1 illustrates a top view of absorbent article in a first configuration according to one embodiment.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Absorbent articles as described herein generally include a moisture-pervious inner layer, an absorbent layer, and a moisture-impervious outer layer. Although the remainder of the description will be specifically directed to adult incontinence articles, a disposable diaper, it is to be understood that the embodiments may also be implemented on other absorbent articles, baby diapers for example, and that the properties and uses described below apply to these other absorbent articles as well.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

In some embodiments, an absorbent article includes a chassis. The chassis has a substantially rectangular shape including a length extending in a longitudinal direction from the back to the front of a user and a width extending in a lateral direction substantially perpendicular to the length between first and second longitudinal edges. The chassis further includes a first portion, a second portion and a crotch portion extending between the first and second portion, a portion of the chassis being configured to absorb fluids. The absorbent article includes a first securement portion operatively coupled to the first portion of the chassis, the first securement portion having a width extending in a lateral direction from the first longitudinal edge of the chassis first portion and a length extending longitudinally along the first longitudinal edge. The absorbent article includes a second securement portion operatively coupled to the second portion of the chassis in a position longitudinally spaced from the first securement portion and configured to releasably attach to the first securement portion. The chassis is configured to include one of a first chassis length or a second chassis length. When the chassis includes the first length, the chassis includes a first width and the first securement portion includes a second width, and when the chassis includes the second length, the chassis includes the first width and the first securement portion includes a third width, greater than the second width.

In some embodiments, an absorbent article includes a chassis. The chassis including a length extending in a longitudinal direction from the back to the front of a user and a width extending in a lateral direction substantially perpendicular to the length between first and second longitudinal edges. The chassis comprises a first portion, a second portion and a crotch portion extending between the first and second portion, a portion of the chassis being configured to absorb fluids. The absorbent article includes a first securement portion operatively coupled to the first portion of the chassis, the first securement portion having a width extending in a lateral direction from the first longitudinal edge of the first portion of the chassis and a length extending longitudinally along the first longitudinal edge. The absorbent article includes a second securement portion having a stretch portion and a non-stretch portion, the second securement portion operatively coupled to the second portion of the chassis in a position longitudinally spaced from the first securement portion and configured to releasably attach to the first securement portion. The chassis configured to include one of a first length or a second length. When the chassis includes the first length, the stretch portion of the second securement portion includes a first width and the non-stretch portion of the second securement portion includes a second width, and when the chassis includes the second length, the stretch portion of the second securement portion includes the first width and the non-stretch portion of the second securement portion includes a third width, greater than the second width.

In some embodiments, a system of absorbent articles to ensure a properly fitting absorbent article includes a first absorbent article and a second absorbent article. The first absorbent article has a first width and a first length along a longitudinal edge. The first absorbent article includes a first portion, a second portion, and a crotch portion extending between the first and second portion. The first absorbent article includes a securement portion operatively coupled to the first portion, the securement portion having a width extending in a lateral direction from the longitudinal edge of the first portion and a length extending longitudinally along the longitudinal edge. The second a second absorbent article has the first width and a second length along a longitudinal edge. The second absorbent article includes a first portion, a second portion, and a crotch portion extending between the first and second portion. The second absorbent article includes a securement portion operatively coupled to the first portion, the securement portion having a width extending in a lateral direction from the first longitudinal edge of the first portion and a length extending longitudinally along the first longitudinal edge.

Other features further provide leg openings that are more generous as a result of the rectangular chassis, rectangular body securement portion configuration allowing for a more accurate fit to accommodate a wide range of body types per article size. Front panels are configured to underlay the back panels providing a more comfortable fit and reduced skin degradation and trauma to the wearer.

FIG. 1 illustrates in plan view, an exemplary non-limiting general embodiment of an absorbent article 100 in a substantially flat un-contracted state (the first configuration), having a reduced component configuration that accommodates multiple sized wearers. In this embodiment the article comprises a chassis 102, securement portions 104, 106, 108, 110, a first core portion 116, and a second core portion 118. Although not shown in this figure, the absorbent article 100 may include a set of leak guards and/or a set leg cuffs 142, 144, both known to those of ordinary skill in the art. In this embodiment there are four body securement portions comprising a first securement portion 104, a second securement portion 106, a third securement portion 108, and a fourth securement portion 110. It should be noted that four securement portions are used in this embodiment however it should be recognized that other embodiments may be configured with more or fewer securement portions.

The absorbent article 100 generally consists of several layers (see, e.g., FIG. 10), including an inner layer, an absorbent layer, and an outer layer. The inner layer faces a wearer and contacts the skin of the wearer when the absorbent article 100 is secured to the wearer. The inner layer may be composed of a moisture-pervious fabric suitable to allow bodily discharge to pass through the inner layer and be absorbed by the absorbent layer. Non-limiting examples of materials suitable to form the inner layer include polypropylene, polyethylene, polyester, materials having hydrophobic properties, combinations thereof and/or the like. Additionally, the inner layer can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The absorbent article 100 generally has a back region 150 and a front region 160. First securement portion 104 and second securement portion 106 are coupled to and may extend from the back region 150, and third securement portion 108 and fourth securement portion 110 are coupled to and may extend from the front region 160. The back region 150 is generally positioned against the back of the user. The front region 160 is generally positioned against the front of the user. The third securement portion 108 and the fourth securement portion 110 are configured to wrap around a wearer's waist from front to back, and the first securement portion 104 and the second securement portion 106 are configured to wrap around a wearer's waist from back to front. In this manner, first securement portion 104 and second securement portion 106 can be coupled to third securement portion 108 and fourth securement portion 110, respectively, to couple the front region 160 to the back region 150.

The absorbent article 100 in this illustration of FIG. 1 is shown with the portion of the absorbent article 100 that contacts the wearer shown facing the viewer. The absorbent article 100 includes a longitudinal axis 101 and a lateral axis 103. The absorbent article 100 includes a first end portion 105, a second end portion 107, and an intermediate portion 109. The first end portion 105 is also referred to herein as a front waist region 105, the second end portion 107 is also referred to herein as a back waist region 107, and is substantially opposite the first end portion 105, and the intermediate portion 109 is also referred to herein as a crotch region 109, and is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer. The back securement portions 104 and 106 and the front securement portions 108 and 110, are separated by distance L1 114. This distance L1 114 defines a portion of the leg opening.

Figure 2A:
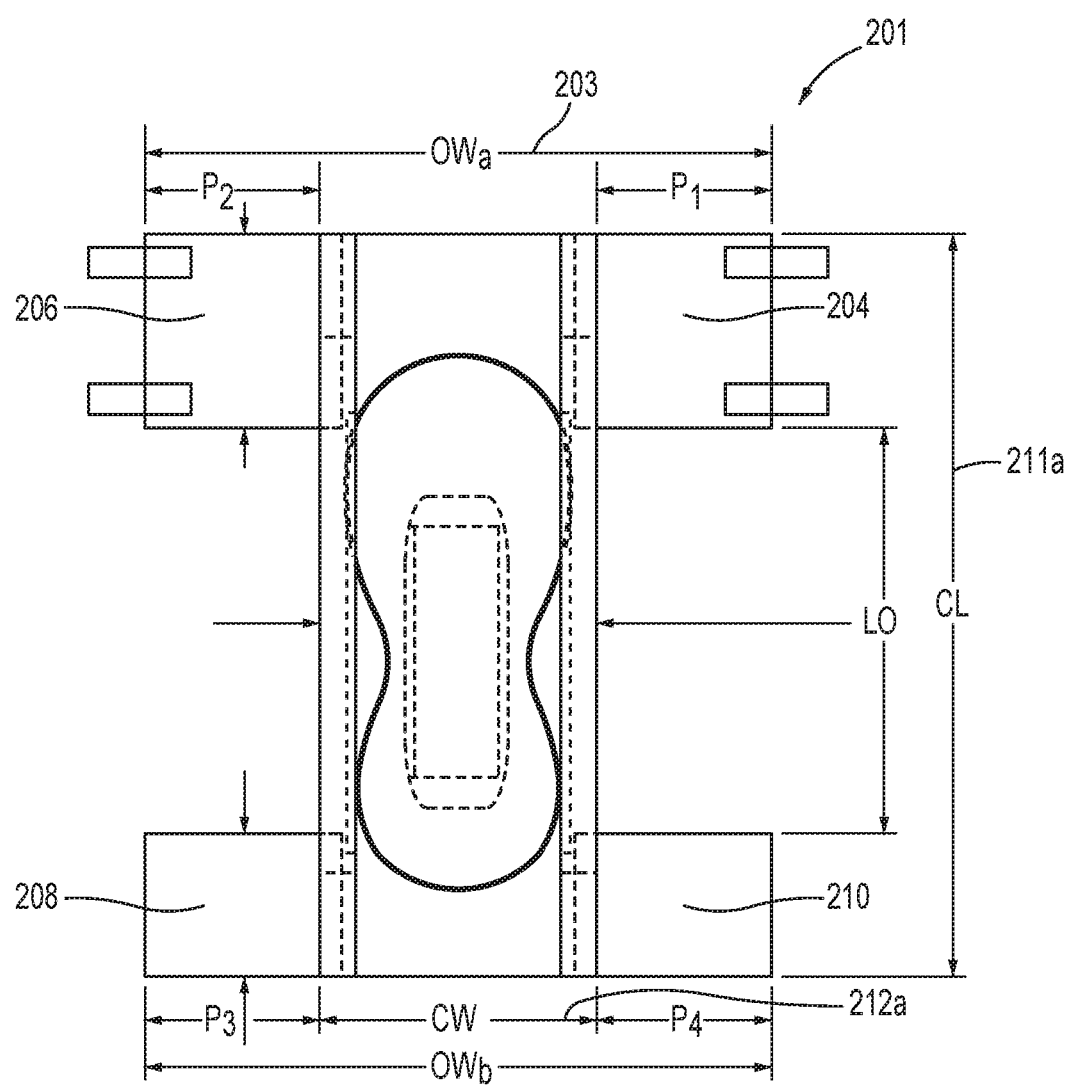
FIG. 2A-B illustrates a top view of a first absorbent article and a second absorbent article in the first configuration according to one embodiment.
Figure 2B:
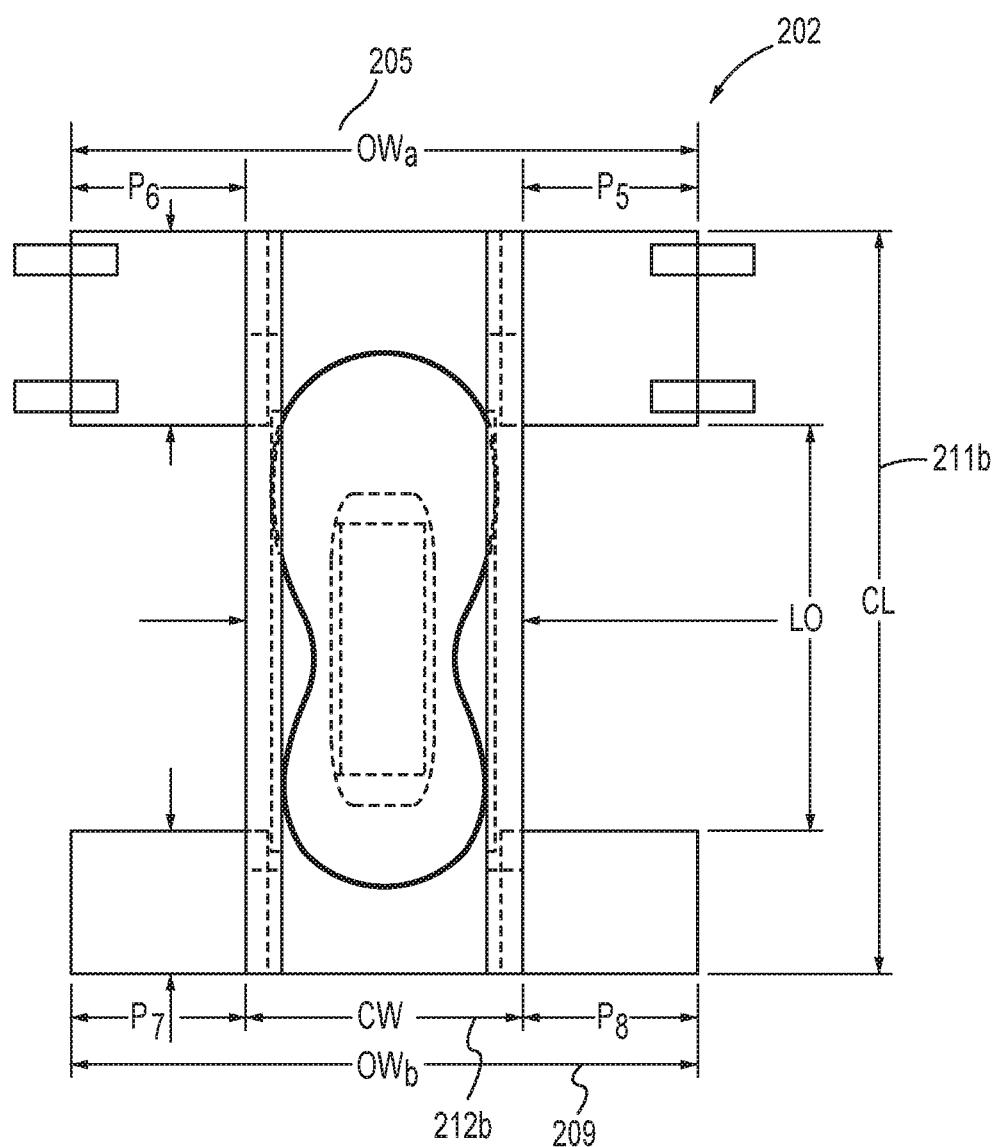
Figure 3A:
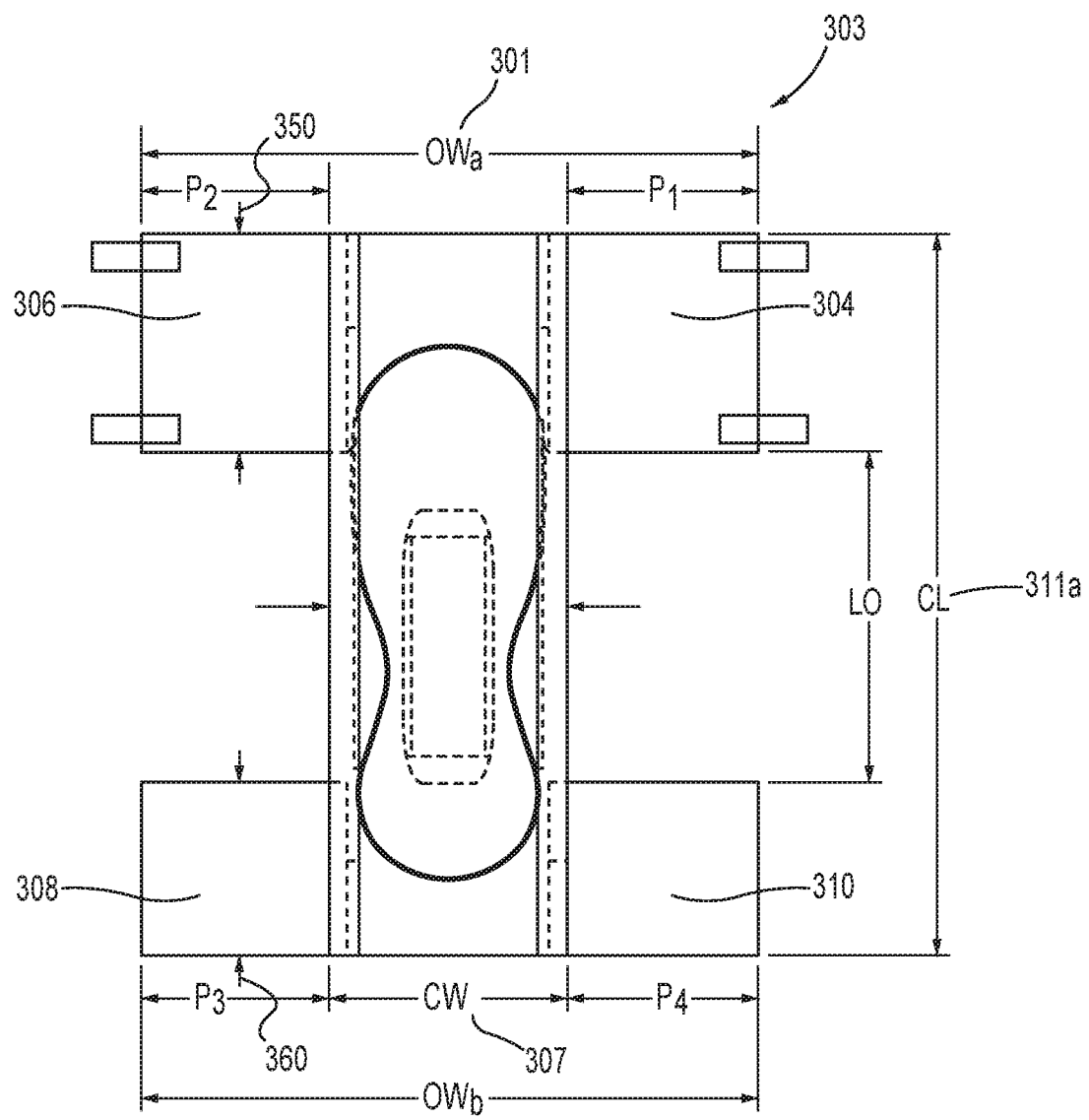
FIG. 3A-B illustrates a top view of a third absorbent article and a fourth absorbent article in the first configuration according to one embodiment.
Figure 3B:
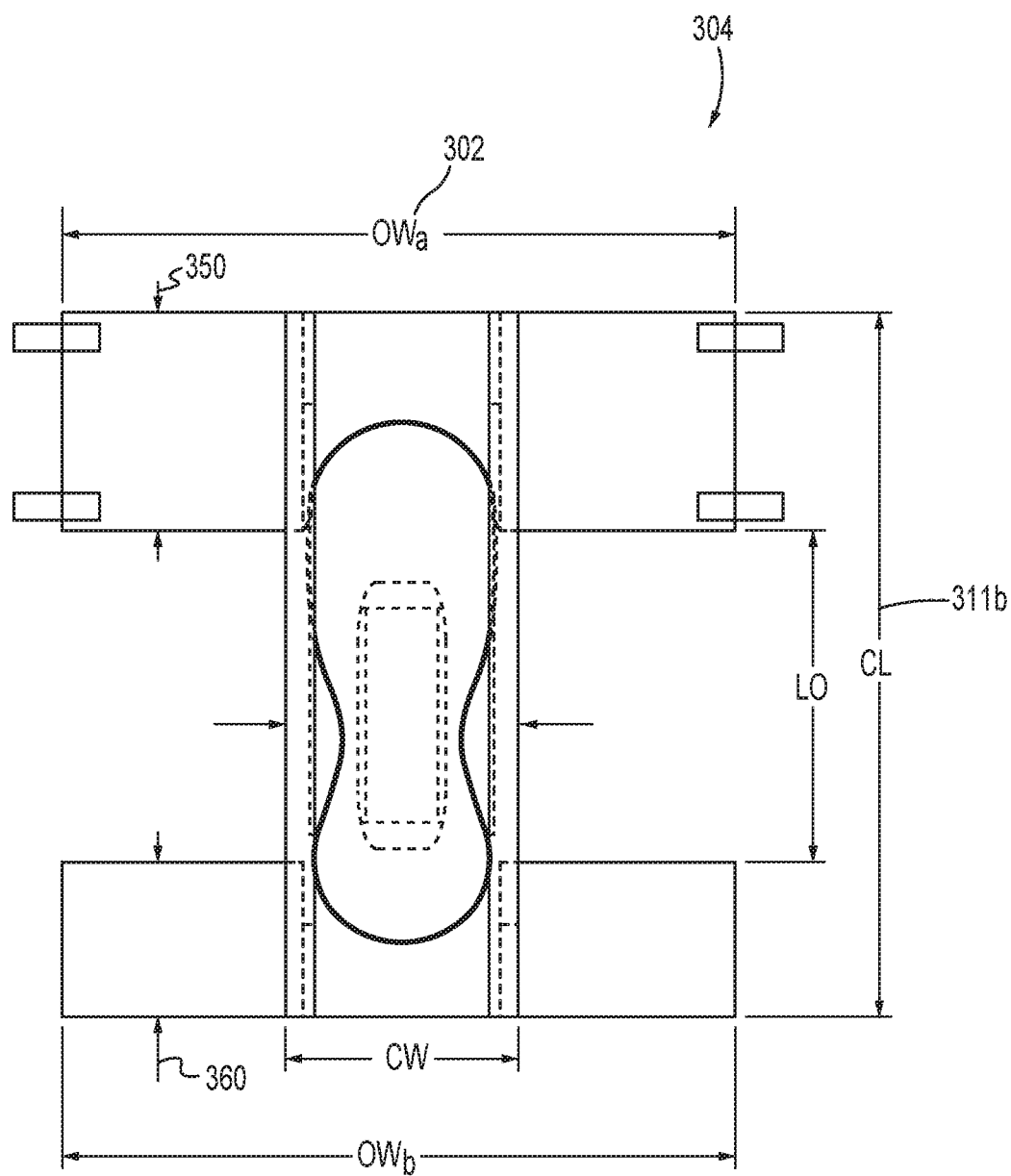

The article's chassis 102 has a chassis width "CW" 112, and a chassis length "CL" 111. The chassis width 112 is a common width across all article sizes that accommodate a plurality of body sizes. Stated in a different way, the absorbent article 100 has a multi-article-size-accommodating width 112 and a multi-article-size-accommodating length 111. Still, put in other words, one chassis width 112 is used for different sized brief articles while still accommodating different wearer's body sizes. By way of example, there are two lengths of the chassis, as illustrated in FIG. 2 and FIG. 3 in combination with FIG. 1, a first chassis length CL 211a, 211b for a first article size and a second article size, in this embodiment a Medium size and a Regular size, and a second chassis length CL 311a 311b for a third article size and a fourth article size, for example a Large size and a X-Large size in this embodiment.

The chassis 102 has a shape such that its outer perimeter is rectangular or at least substantially rectangular in the first configuration in this embodiment the absorbent article 100 has at least one securement portion that is coupled to the chassis 102 at one of the front waist region 105 or the back waist region 107. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hour glass shapes, T-shapes, and the like.

Figure 7:
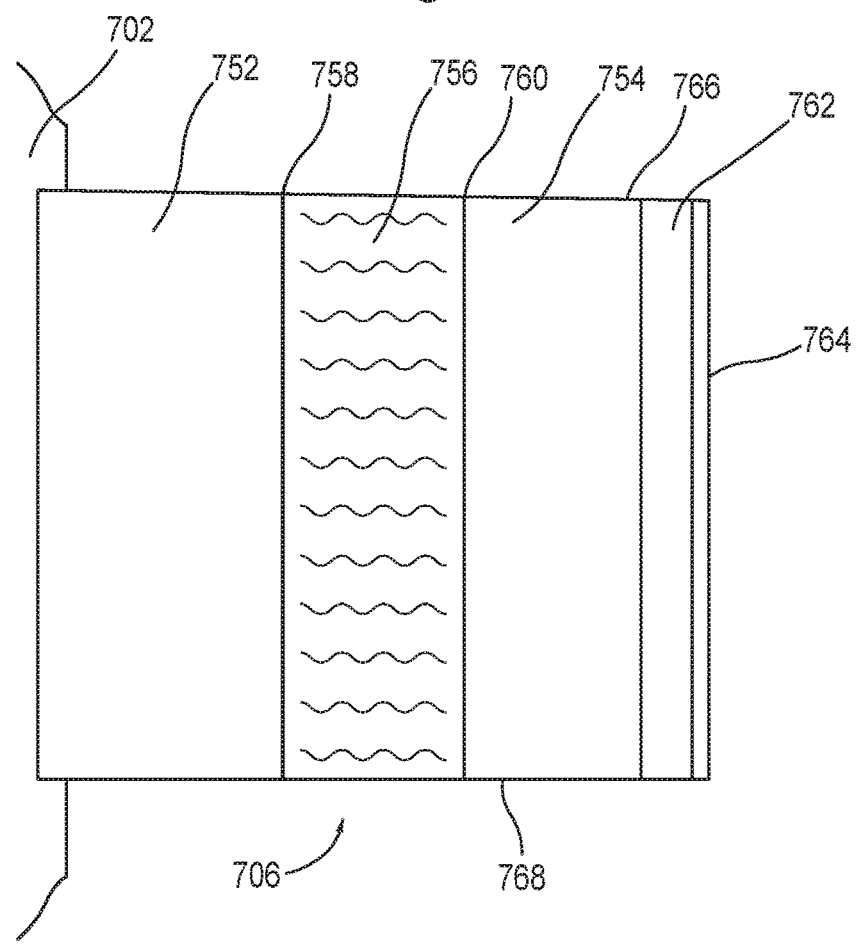
FIG. 7 illustrates a securement portion having an elastic panel according to one embodiment.

The first securement portion 104 is coupled to a first longitudinal side edge portion 113 of the chassis, the first securement portion 104 overlapping the chassis 102 along the lineal contact points of attachment 132. The amount of overlap is sufficient to reliably attach the securement portion to the chassis such that there is no separation during use, as would be understood to one of ordinary skill in the art. In one embodiment, the overlap of the first securement portion 104 with the chassis 102 longitudinal side edge 113 is between 6 mm and 50 mm (or about 0.25 inches and 2.0 inches). In this embodiment, the overlap of the securement portion with the chassis is generally the same for all four securement portions. First securement portion 104 includes two fasteners 120. Fasteners 120 can be configured to operatively couple first securement portion 104 to third securement portion 108 and/or to anywhere along the front region 105. While FIG. 1 depicts first securement portion 104 as including two fasteners 120, in some embodiments, first securement portion 104 can include more or fewer fasteners. While FIG. 1 depicts fasteners 120 sized and shaped a particular way, in other embodiments, fasteners 120 can be a different size and/or shape, such as, for example, similar to fastener 762 as depicted in FIG. 7.

The second securement portion 106 is coupled to the second longitudinal side edge portion 115 of the chassis, the first securement portion 106 overlapping the chassis 102 along the lineal contact points of attachment 130, in the same manner as the first securement portion 104. Together, the first securement portion 104, the back waist region of the chassis 107, and the second securement portion 106, laterally form the overall width "$OW_a$," 170 of the article at the back region. The first securement portion 104 has a first width $P_1$ 122 and the second securement portion 106 has a second width $P_2$ 124. Second securement portion 106 includes two fasteners 120. Fasteners 120 can be configured to operatively couple second securement portion 106 to fourth securement portion 110 and/or to anywhere along the front region 105. While FIG. 1 depicts second securement portion 106 as including two fasteners 120, in some embodiments, second securement portion 106 can include more or fewer fasteners. While FIG. 1 depicts fasteners 120 sized and shaped a particular way, in other embodiments, fasteners 120 can be a different size and/or shape, such as, for example, similar to fastener 762 as depicted in FIG. 7.

In some embodiments, the first securement portion 104 and the second securement portion 106 can be coupled to the chassis 102 in the following manner. An end portion 131 of first securement portion 104 can be temporarily coupled to and end portion 129 of second securement portion 106. In some of these embodiments, end portion 131 can overlap end portion 129 and can be temporarily coupled to end portion 129 via an adhesive. In other of these embodiments, end portion 131 can be temporarily coupled to end portion 129 via a perforated seem (not shown) between end portion 129 and end portion 131. Chassis 102 can be temporarily coupled to first securement portion 104 and second securement portion 106. Specifically, the back waist region 107 of the chassis 102 can be disposed substantially on top of the end portion 129 of the first securement portion 104 and the end portion 131 of the second securement portion 106. Said another way, end portion 129 of first securement portion 104 and end portion 131 of second securement portion 106 can be disposed on a first side of chassis 102. At least a portion of first securement portion 104 can be folded over chassis 102 such that first securement portion 104 can be operatively coupled to chassis 102 approximately at lineal contact points 132 as described above. At least a portion of second securement portion 106 can be folded over chassis 102 such that second securement portion 106 can be operatively coupled to chassis 102 approximately at lineal contact points 130 as described above. End portion 129 and end portion 131 can be released from contact with the other of end portion 129 and end portion 131.

The third securement portion 108 is coupled to a third longitudinal side edge portion 119 of the chassis, the third securement portion 108 overlapping the chassis 102 along the lineal contact points of attachment 134. The amount of overlap is sufficient to reliably attach the securement portion to the chassis such that there is no separation during use, as would be understood to one of ordinary skill in the art.

The fourth securement portion 110 is coupled to the fourth longitudinal side edge portion 121 of the chassis, the first securement portion 110 overlapping the chassis 102 along the lineal contact points of attachment 136, in the same manner as the first, second or third securement portion 104, 106, 108. Together, the third securement portion 108, the front waist region of the chassis 105, and the fourth securement portion 110, laterally form the overall width "$OW_b$," 180 of the absorbent article 100 at the front region. The third securement portion 108 has a third width $P_3$ 126 and the fourth securement portion 110 has a fourth width $P_4$ 128. In this embodiment all four securement portion widths $P_1$-$P_4$ are substantially the same.

Third securement portion 108 and fourth securement portion 110 can be operatively coupled to the chassis 102 via temporary coupling of end portion 138 of third securement portion 108 and end portion 139 of fourth securement portion 110 in a manner similar to that described above with reference to first securement portion 104 and second securement portion 106.

In other embodiments the width of the securement portions may vary from portion to portion as well as from front to back or side to side. For example, the first securement portion 104 and the second securement portion 106 may have a substantially equal width but a different width than the third securement portion 108 and the fourth securement portion 110. In another embodiment the first securement portion and the second securement portion are one continuous piece, running across the entire chassis in a perpendicular fashion and extending beyond the edges of the chassis, forming the body securement portions. In another embodiment the third securement portion and the fourth securement portion are one continuous piece, running across the entire chassis in a perpendicular fashion and extending beyond the edges of the chassis, forming the body securement portions. In one embodiment the overall width of the back region "$OW_a$" 170, including the first securement portion 104, the chassis 102 and the second securement portion 106 stays the same, and similarly the overall width of the front region "$OW_b$," 180, including the third securement portion 108 the chassis 102 and the fourth securement portion 110 stays substantially the same.

In one embodiment the chassis 102 has a common chassis width CW 112 between 190 mm and 350 mm and preferably about 320 mm for all article sizes (the first size article, the second size article, the third size article and the fourth size article). In this embodiment the width of each securement portion ($P_x$) is the same at the back region end 150 as it is in the front region end 160. For all article sizes (e.g. medium, regular, large extra large), the chassis width 112 is the same. In this embodiment the chassis 102 has a rectangular shape or a substantially rectangular shape, wherein the width is the short dimension. For the first article size and the second article size, the chassis 102 may also have a first common chassis length CL 111 which in this embodiment is between 800 mm and 880 mm and preferably 860 mm. For the third article size and the fourth article size, the chassis 102 may have a second common chassis length CL 111, different from the first common chassis length, and in this embodiment is between 860 mm to 1000 mm and preferably 960 mm. The Chassis length CL 111 in this figure refers to the dimension and not the actual value.

As shown in FIG. 1, the edge 119 of chassis 102 can be substantially flush with edge 117 of portion 104 and portion 106. In some embodiments, the edge 119 can extend beyond the edge 117 of portion 104 and portion 106 (see, e.g., FIG. 4).

The articles are assembled together in the manufacturing process such that the body securement portions are secured to the chassis 102 wherein the panels 104, 106, 108 and 110 are disposed between a first chassis layer, for example a top sheet, and a second chassis layer, for example a bottom sheet. The machine assembling the article is set such that the panel widths are changed from a first width to a second width in order to change over from building a first article size 201 to a second article size 202. Similarly, when changing over to a third article size, the panel widths are increased, and additionally in this embodiment, the chassis length is increased to the second chassis length as for the third article size 303 and fourth article size 304. For these changes, the changeover is completed by running different programs in the machine and minimal or even zero hard tooling change over is required. By way of example, there may be no hard tool changeovers such as the replacement of cutting dies which are typically used for cutting leg openings. Instead, only vacuum plate changes may be needed for the size changes in the panel widths and length which are relatively simple replacements. In some embodiments, the vacuum plates need not even be physically replaced, the vacuum plates are sized to accommodate all sizes of panels and depending on the size of the panel, and vacuum ports are enabled or disabled based on the size of the panel.

FIG. 2 and FIG. 3 illustrate together, in plan view fashion, an exemplary non-limiting general embodiment of four different sized absorbent articles, in the flat un-contracted state. The first absorbent article 201 configured as a first wearer size and the second absorbent article 202 configured as a second wearer size are shown in FIG. 2. The third absorbent article 303 sized as a third wearer size and the fourth absorbent article 304 sized as a fourth wearer size are shown, in their flat un-contracted state, in FIG. 3. The different wearer sizes, the first and second articles 201, 202 are created by configuring the securement portion widths, e.g. P1, P2 or both, for the first wearer size 201 and the second wearer size 202 in order to accommodate different wearer waist sizes, all with the same chassis width 212 and chassis length 211a and 211b. For example, the first size article 201 will have a fixed chassis width "CW" of about 320 mm and first, second, third and fourth securement portion individual widths of about 180 mm, while the second size article will have first, second, third and fourth securement portion widths of about 200 mm, however still with the chassis width "CW" of 320 mm. The chassis length 211a and 211b, are about 860 mm for the first and second articles 201, 202.

In this embodiment, using the first size article 201 as an example, the securement portion width "$P_x$" may be maintained the same for each securement portion 204, 206, 208, 210 or in another embodiment the first securement width 204 may be a different width than the second securement portion width 206, while maintaining the same overall width 203 of the rear portion of the article. In yet another embodiment the first and second securement portions 204, 206, may have a first width, and the third and fourth securement portions 208, 210 may have a second width.

For the third size 303 and the fourth size 304 (FIG. 3), the chassis width 311a and 311b "CW" of about 320 mm, remains the same as the first and second sizes, however the securement portion widths "$P_x$" and the chassis lengths "CL" 111 are configured differently from the first size 201 and the second size 202 to accommodate the different, greater in this embodiment, article sizes. The third size article 303 will have a fixed chassis width "CW" of about 320 mm and first, second, third and fourth securement portion widths of about 255 mm, while the fourth size article 304 will have first, second, third and fourth securement portion widths of about 275 mm. The chassis length, 311a and 311b may be between 860 mm and 1000 mm and in one embodiment the chassis length 311a and 311b, is about 960 mm for the first and second articles 201, 202.

As with the first and second article sizes 201, 202, the securement portion width "$P_x$" may be maintained the same for each securement portion 304, 306, 308, 310 or in another embodiment the first securement portion 304 width may be a different width than the second securement portion width 306, yet while maintaining the same overall width "$OW_a$" 301 of the article at the back end or the same overall width "$OW_b$," 302 of the article at the front end. In yet another embodiment the first and second securement portions 304, 306, may have a first width, and the third and fourth securement portions 308, 310 may have a second width. As the width of the first and second portions increases, the width of the third and fourth portion may decrease, so long as there is overlap in accordance with the size of the article to fit the wearer.

In the embodiment shown in FIG. 3, the third size article 303 will have a fixed chassis width "CW" of about 320 mm and first, second, third and fourth securement portion widths of about 255 mm, while the fourth size article 304 will have first, second, third and fourth securement portion widths of about 275 mm. The chassis length, 311a and 311b may be between 860 mm and 1000 mm and in one embodiment the chassis length 311a and 311b, is about 960 mm for the first and second articles 201, 202.

Figure 4:
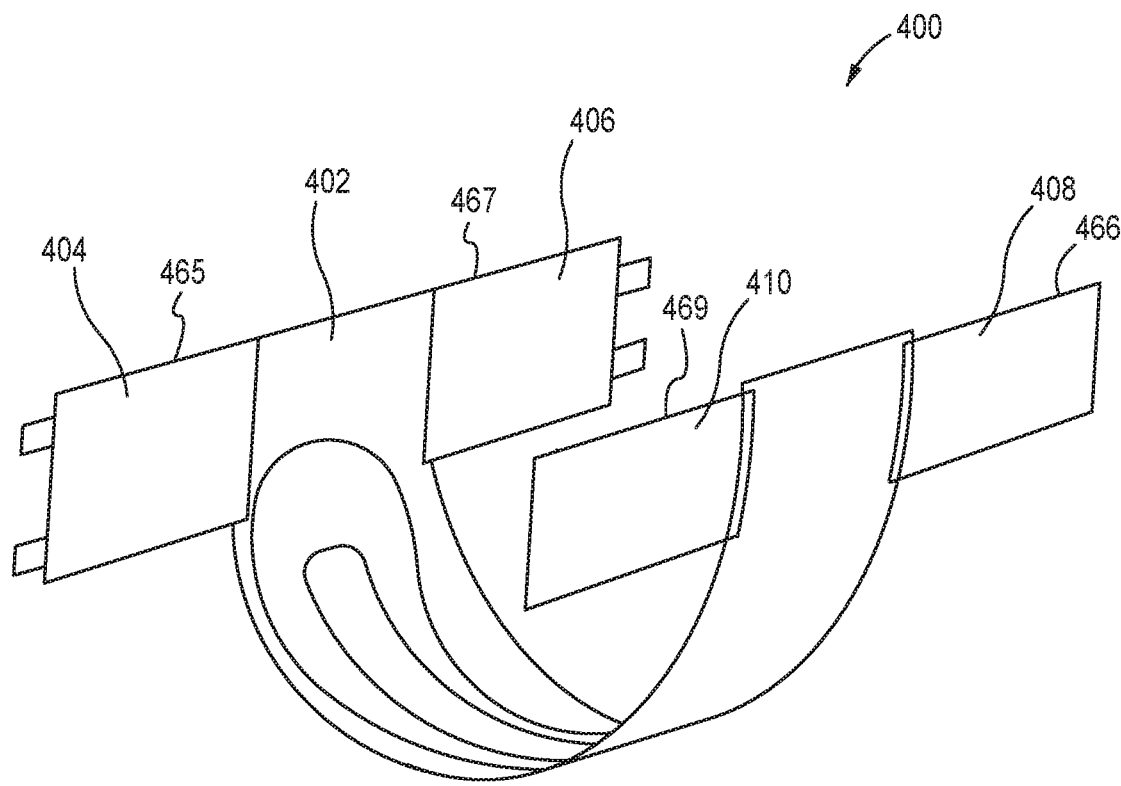
FIG. 4 illustrates a perspective view of an absorbent article in a second configuration.

FIG. 4 is a perspective view of an absorbent article 400 in a second configuration. Absorbent article 400 can be similar to and include similar components as absorbent article 100. By way of example, absorbent article 400 includes securement portion 404, 406, 408, and 410, which can be similar to securement portions 104, 106, 108, and 110, respectively. The second configuration shows the chassis 402 in a position as it would be when placed on the wearer although the securement portions, 404, 406, 408 and 410 remain in an un-contracted, unwrapped state. Securement portion 404 includes an edge 465, securement portion 406 includes an edge 467, securement portion 408 includes an edge 466, and securement portion 410 includes an edge 469.

Figure 5:
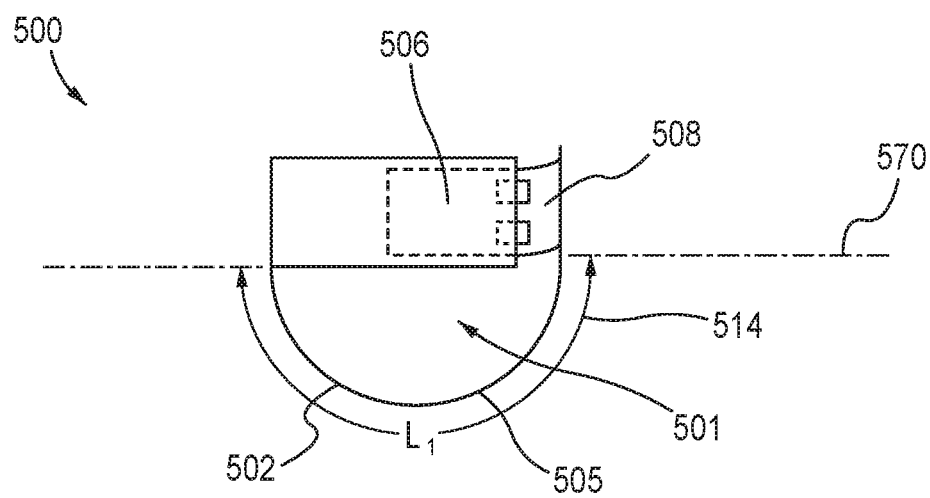
FIG. 5 illustrates a side view of an absorbent article in a third configuration.

FIG. 5 is a side view of an absorbent article 500 in a third configuration. Absorbent article 500 can be similar to and include similar components as absorbent article 100. By way of example, absorbent article 500 includes securement portion 504 (not shown), 506, 508, and 510 (not shown), which can be similar to securement portions 104, 106, 108, and 110, respectively. The third configuration shows the securement portions in a wrapped state, as they would be wrapped around a wearer. In this embodiment, the securement portions may be configured such that the second securement portion 506 overlaps the third securement portion 508, and the first securement portion 504 overlaps the fourth securement portion 510. The third and fourth securement portions 508, 510, lay directly adjacent the wearer's skin, while the first securement portion 504 and the second securement portion 506, lie partially on the wearer's skin and partially on the third and fourth securement portions respectively. Having front securement portions that may wrap substantially up to an in some embodiments substantially past a person mid point and around towards and against the wearer's backside provides a more comfortable fit.

The leg opening 501, is defined by a bottom edge 570 of the securement portions, a second securement portion 506 and a third securement portion 508, and the longitudinal edges portions 505 of the chassis 502, having the length L1 114 between the securement portions along the longitudinal edge of the chassis 502. Because of the rectangular nature of the securement portions 506 and 508 for the first leg opening, the bottom edge 570 is significantly adjacent the waist and, is positioned higher than or at least significantly above the thigh of the wearer.

Figure 6:
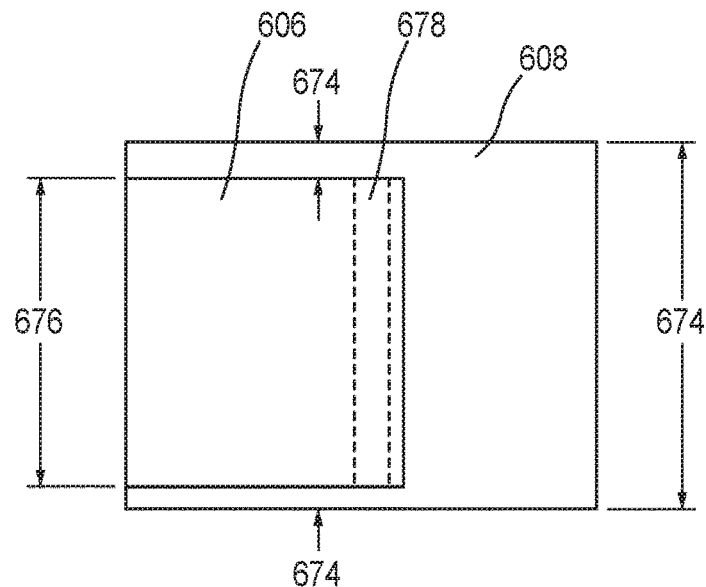
FIG. 6 illustrates a front securement portion coupled to a back securement portion according to one embodiment.

FIG. 6 illustrates a front securement portion 608 and a back securement portion 606. The front securement portion 608 can be similar to third securement portion 108 and fourth securement portion 110, and back securement portion 606 can be similar to first securement portion 104 and second securement portion 106. The front securement portion has a length 674 and the back securement portion has a length 676. The length of the front securement portion 608 is greater than the length 676 of the back securement portion. A fastener 678 is coupled to the back securement portion 606. The length of the front securement portion 608 is greater than the length for the back securement portion 606 to move up or down during fastening and still provide a landing zone for the fastener 678, such that the fastener 678 does not come in contact with the wearer's skin. In this embodiment, the fastener 678 has substantially the same length as the back securement portion 606 length 676. The fastener 678 in this embodiment may be applied to the back securement portion 606 and cut to length during the formation of the back securement portion 606.

FIG. 7 illustrates a securement portion 706, of a chassis 702, the securement portion 706 including an elastic panel coupled thereto. Securement portion 706 can be similar to and include similar components with first securement portion 104 and second securement portion 106. In one embodiment, the securement portion 706 has a first non-elastic panel 752, a second non-elastic panel 754 and an elastic panel 756. In one embodiment, the elastic panel 756 is disposed between the first non-elastic panel 752 and the second non-elastic panel 754. Each panel has a first side edge and a second side edge, distal the first side edge, and a top edge 766 and a bottom edge 768, forming a rectangle. The first non-elastic panel 752 is attached to the chassis 702 at a first side edge of the first non-elastic panel 752 and to a first side edge of the elastic panel 756 at a second side edge, distal the first side edge. A second side edge of the elastic panel 756, distal the first side edge, is coupled to a first side edge of the second non-elastic panel 754. The second side edge 764, distal the first side edge, has at least one fastener 762 coupled thereto. Securement portion 706 is coupled to the chassis 702 in a similar fashion to the securement portions 104, 106, 108, 110 as discussed above.

A first seam 758 is formed by the first non-elastic panel 752 second side edge joint with the first side edge of the elastic panel 756. A second seam 760 is formed by the second side edge of the elastic panel 756, joint with the first side edge of the second non-elastic panel 754.

Having a portion of the securement portion 706 include a stretchable material allows for a single article to fit a greater number size rage of wearers. For example in one embodiment, only two article sizes are needed to fit the same size range of wears for the four articles discussed above. This further reduces waste as there is a reduction in the amount of machinery needed to build multiple size accommodating articles as well as less change over from product size to product size, thereby increasing efficiency in the manufacturing process.

In one embodiment the elastic panel 756 has a width between 40 mm and 100 mm and preferably has a width of about 68 mm in one embodiment for a first article size. The non-elastic portions may have equal widths which may be about 77 mm for example for the first article size. For a second size in this embodiment, the elastic panel 756 has a width between 40 mm and 100 mm and preferably has a width of about 68 mm in one embodiment for a first article size. The non-elastic portions may have equal widths which may be about 108 mm for example. There is an overlap of the non-elastic portion and the elastic portion of about 15 mm in this embodiment. This overlap is where the two portions are joined together. In this embodiment, the two portions are glued together. One of ordinary skill in the art will understand the plurality of methods and procedures for affixing the portions together.

The stretch material may be made from stretch material as understood by those of ordinary skill in the art. In one embodiment the stretch material is a 107 GSM stretch material by 3M.

Figure 8:
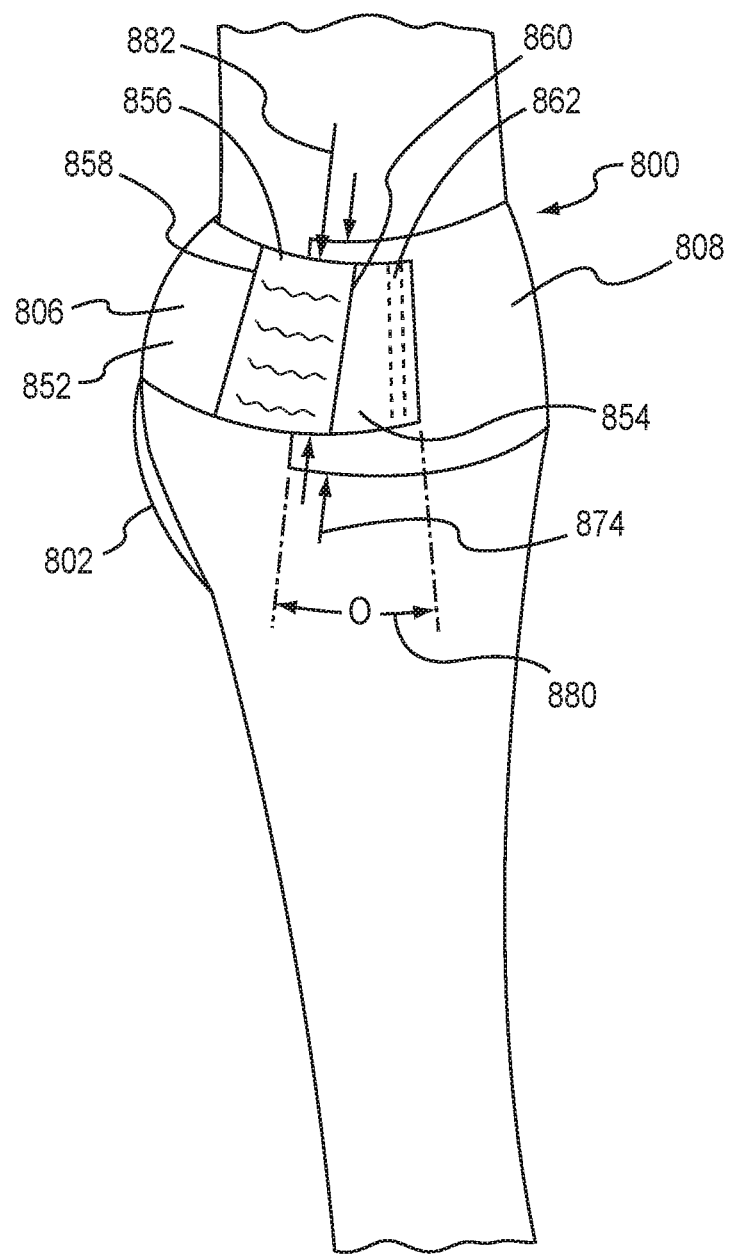
FIG. 8 illustrates a wearer including an absorbent article in the third configuration according to one embodiment.

FIG. 8 illustrates a further embodiment of an absorbent article 800 as used by a wearer. The absorbent article can include a chassis 802. In this embodiment a front securement portion 808 wraps around the wearer from front to back and lays underneath the back securement portion 806. The back securement portion 806 can overlap the front securement portion 808 a distance O 880. Front securement portion 808 can be similar to and include similar components with third securement portion 108, fourth securement portion 110, and front securement portion 708. Similarly, back securement portion 806 can be similar to and include similar components with first securement portion 104, second securement portion 106 and back securement portion 706. In this embodiment the front securement portion 808 length 874 is greater than the back securement portion 806 length 882. The back securement portion 806 includes an elastic panel 856 disposed between a first non-elastic panel 852 and a second non-elastic panel 854, and includes a fastener 862 similar to fastener 762 and fastener 678. A first seam 858 is formed by the joint between the elastic portion 856 and the first non-elastic portion 852. A second seam 868 is formed by the joint between the elastic portion 856 and the second non-elastic portion 854. The width of the front securement portion 808 is great enough that it lies between the second seam 860 and the wearer's skin reducing the abrasive effect of the seam on the skin. In this embodiment the front securement portion width is between 130 mm and 260 mm and is preferably 180 mm for a first embodiment first size. The overall width for the first size is 680 mm, and may be between 630 mm and 830 mm. The front securement portion width is between 205 mm and 335 mm and is preferably 255 mm for a first embodiment second size. The overall width for the second size is 829 mm, and may be between 720 mm and 950 mm.

Figure 9:
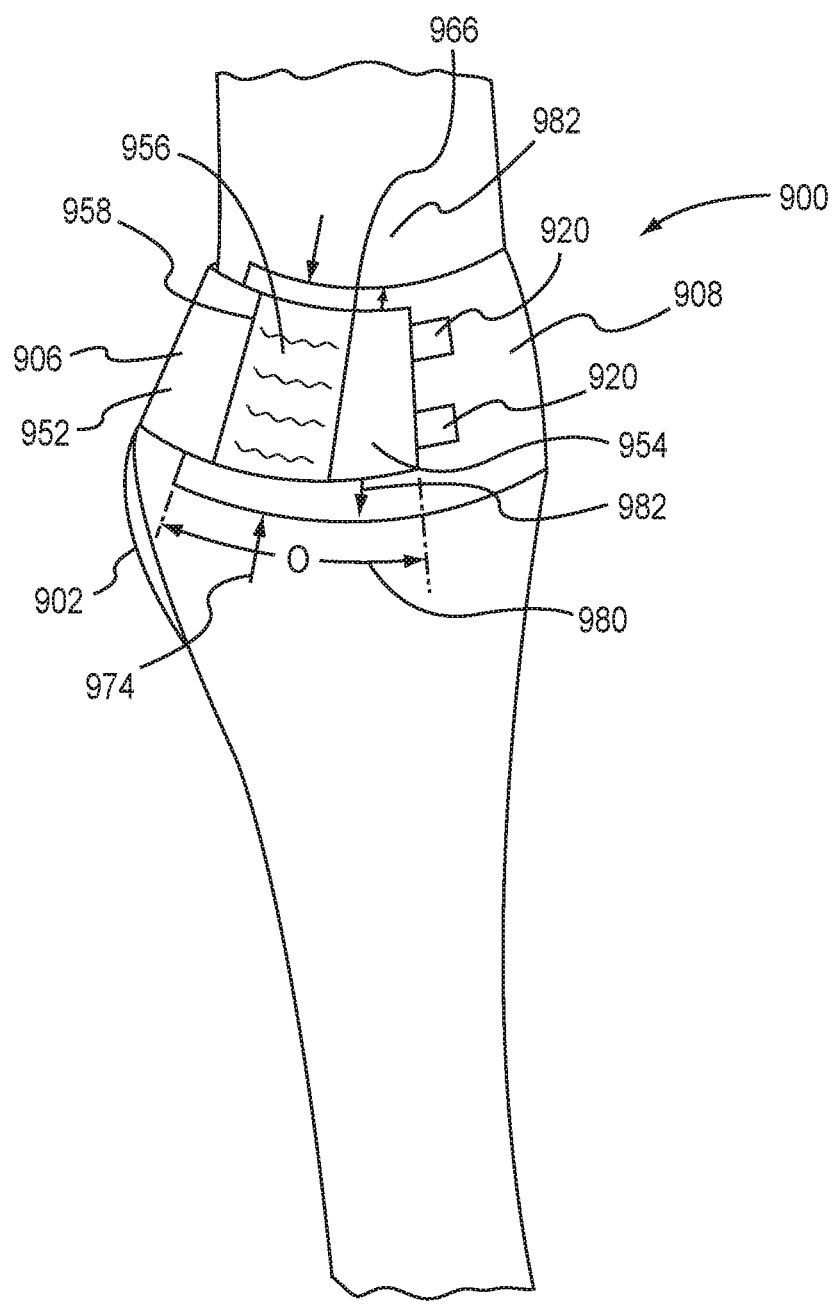
FIG. 9 illustrates a wearer including an absorbent article in the third configuration according to another embodiment.

FIG. 9 illustrates a wearer including an absorbent article 900 in the third configuration. In this embodiment a front securement portion 908 wraps around the wearer from front to back and lays underneath the back securement portion 906. The back securement portion 906 can overlap the front securement portion 908 a distance 980. Front securement portion 908 can be similar to and include similar components with third securement portion 108, fourth securement portion 110, and front securement portion 708. Similarly, back securement portion 906 can be similar to and include similar components with first securement portion 104, second securement portion 106 and back securement portion 706. In this embodiment the front securement portion 908 length 974 is greater than the back securement portion 906 length 982. The back securement portion 906 includes an elastic panel 956 disposed between a first non-elastic panel 952 and a second non-elastic panel 954, and includes a fastener 920 similar to fastener 120. A first seam 966 is formed by the joint between the elastic panel 956 and the second non-elastic panel 954. The width of the front securement portion 908 is great enough that it lies between the first seam 966 and the wearer's skin reducing the abrasive effect of the seam on the skin. A second seam 958 is formed by the joint between the elastic panel 856 and the first non-elastic panel 852. The width of the front securement portion 908 is great enough that it lies between the first seam 966 and the second seam 958 and the wearer's skin reducing the abrasive effect of the seam on the skin.

In this embodiment the front securement portion width is between 130 mm and 260 mm and is preferably 180 mm for a first embodiment first size. The overall width for the first size is 680 mm, and may be between 630 mm and 830 mm. The front securement portion width is between 205 mm and 335 mm and is preferably 255 mm for a first embodiment second size. The overall width for the second size is 829 mm, and may be between 720 mm and 950 mm.

Figure 10:
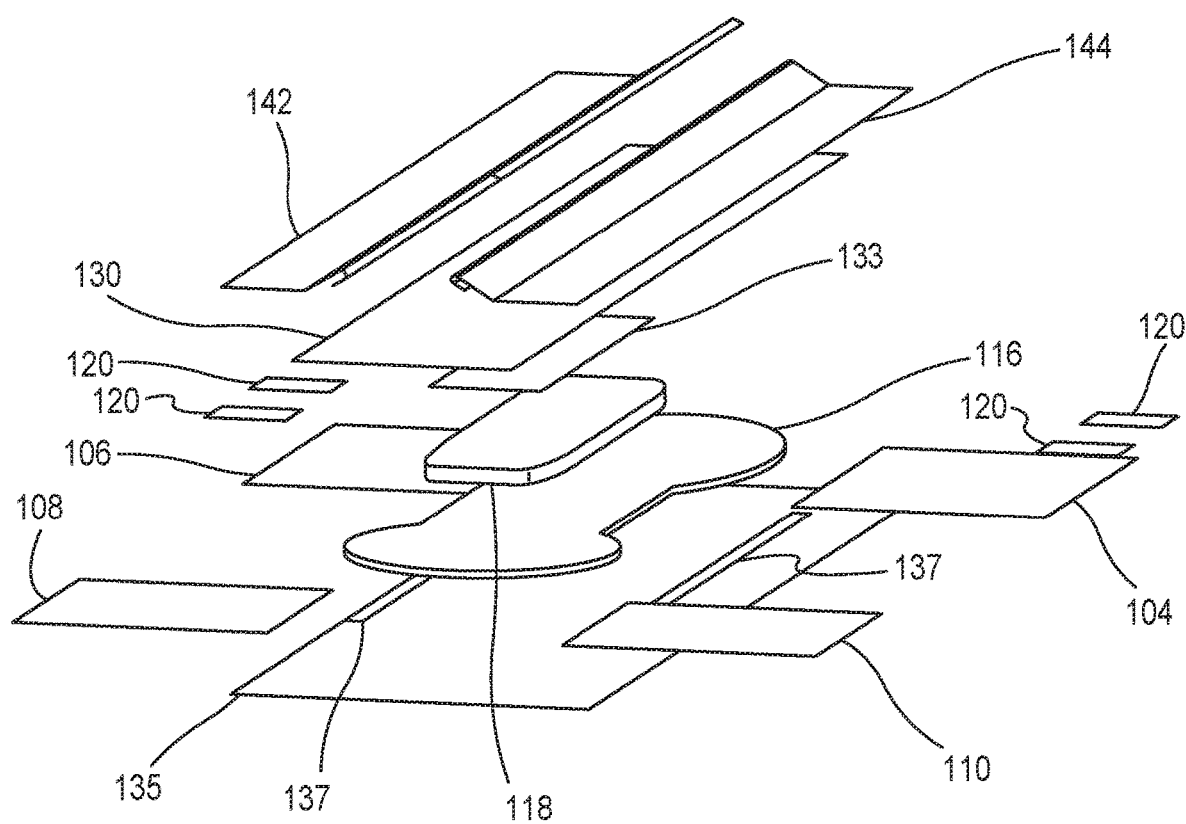
FIG. 10 illustrates an exploded view of the absorbent article shown in FIG. 1.

FIG. 10 is an exploded perspective view of the absorbent article 100 with certain items removed for clarity. As shown in FIG. 10, absorbent article 100 includes securement portions 104, 106, 108, 110; first core 116; second core 118; fasteners 120; and leg cuffs 142, 144. Additionally, absorbent article includes an inner layer 130, an absorbent core 133 disposed between the inner layer 130 and the second core 118, an outer layer 135, and elastic bands 137. The elastic bands 137 can improve the fit of the absorbent article 100 and can improve the comfort of the wearer.

Figure 11:
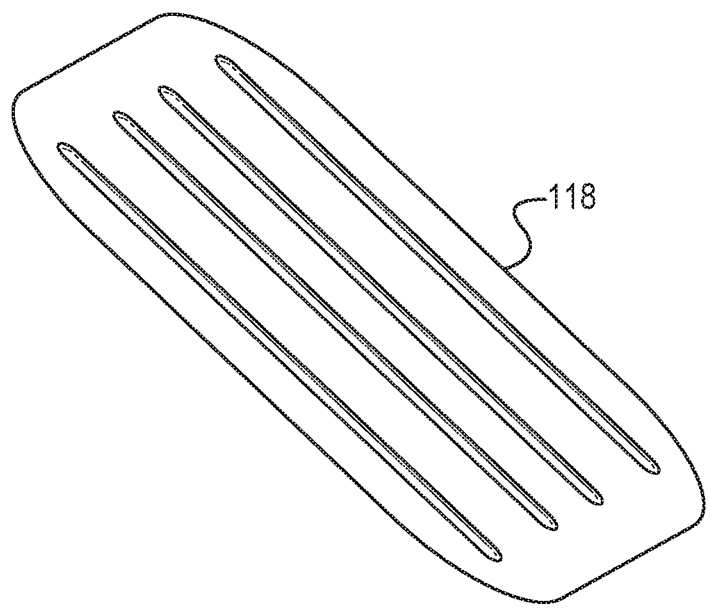
FIG. 11 illustrates a perspective view of a second core of the absorbent article depicted in FIG. 1.
Figure 12:
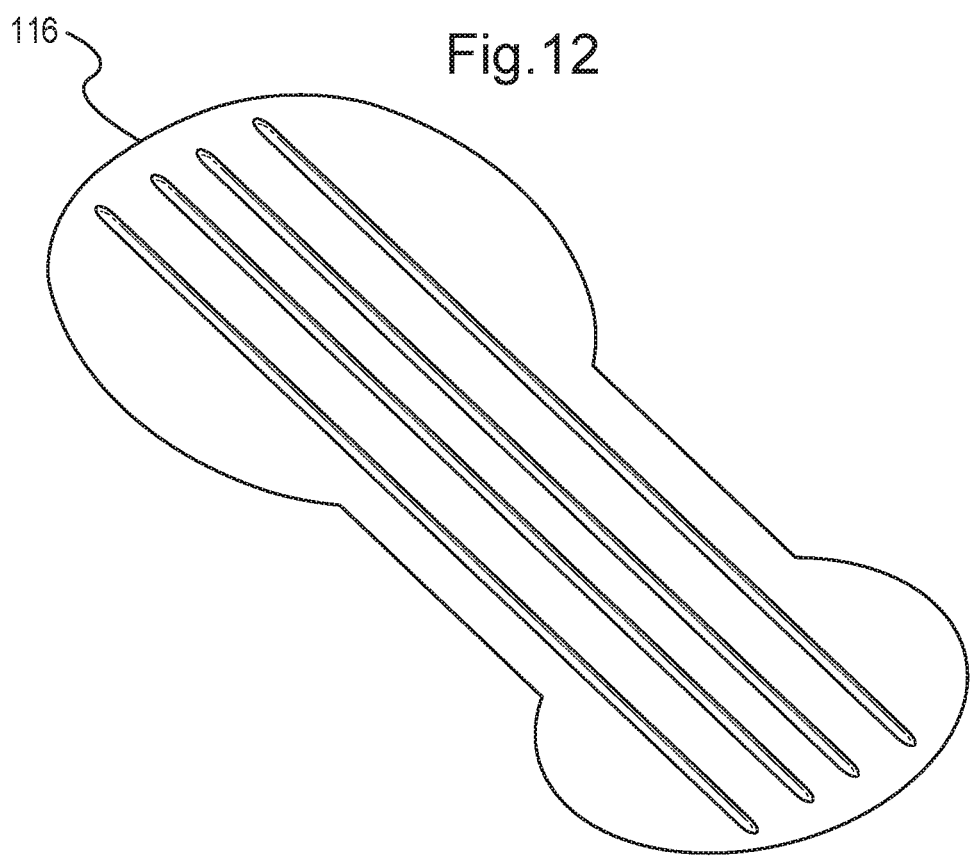
FIG. 12 illustrates a perspective view of a first core of the absorbent article depicted in FIG. 1.

FIG. 11 is a perspective view of a top side (facing towards wearer) of the second core 118, and FIG. 12 is a perspective view of a bottom side (facing away from a wearer) of the first core 116. Each of first core 116 and second core 118 can be composed of similar material, and can be shaped depending on the size of the absorbent article, and whether it is indented for use by infants, children and/or adults. By way of example, and as shown in FIGS. 11 and 12, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer (SAP), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 11 and 12 depict the first core 116 having an embossed bottom, and the second core 118 having an embossed top (see also, for example, FIGS. 15 and 16), in some embodiments, an absorbent article can have only a single core with no embossing (see, e.g., FIG. 13), a single core with embossing on both sides (see, e.g., FIG. 14), and/or other combinations of one or two cores each with embossing on one, both, or neither side. While the FIGS. show absorbent articles include one or two cores, in some embodiments, absorbent articles can include more or fewer cores. While FIGS. 11, 12, 14, and 15 depict embossing as including four spaced apart embossing "lines," in some embodiments, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 11, 12, 14, and 15 depict embossing substantially along the entire width and length of each respective core, in some embodiments a core can have embossing substantially along an entire width and/or length, and/or a portion of a width and/or length.

Figure 13:
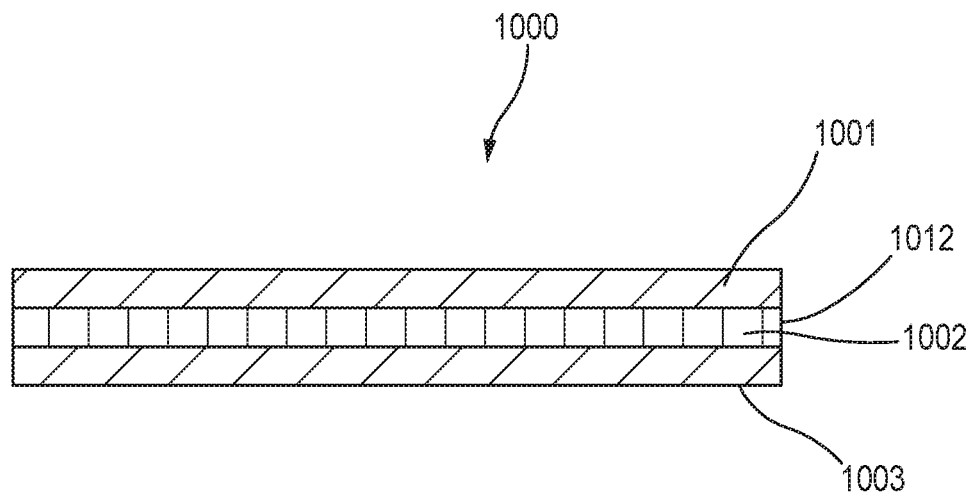
FIG. 13 illustrates a cross-section of an end view of a portion of an absorbent article according to an embodiment.

FIG. 13 is a cross-sectional view of a portion of an absorbent article 1000. The absorbent articles described above generally consists of several layers including an inner layer 1001, an absorbent layer 1002, and an outer layer 1003, as depicted in FIG. 10. In general and applicable to any of the above embodiment, an absorbent layer 1002 may be positioned between the inner layer 1001 and the outer layer 1003 of the absorbent article. The absorbent layer 1002 includes a core 1012. The core 1012 can be similar to and include similar characteristics with one or both of first core 116 and/or second core 118.

The outer layer 1003, which faces away from the wearer when the absorbent article is secured to the wearer, is composed of a moisture-impervious fabric. Accordingly, the outer layer 1003 may be made of any material suitable to minimize or prevent fluids and other discharge from escaping the diaper. Non-limiting examples of suitable materials for the outer layer include polyethylene and/or breathable poly. According to some embodiments, the outer layer can be a thin film such as, for example, polyethylene film. As will be discussed in greater detail below, the outer layer is typically formed from a plastic resin of any of the above-referenced materials. This outer layer 1003 that prevents diapers from leaking also prevents air circulation, thus creating a warm, moist environment where bacteria and fungi can thrive. This bacteria and fungi can cause infectious diseases, unpleasant odors, urinary tract infections, bladder infections, kidney infections, diaper rashes and the like.

Figure 14:
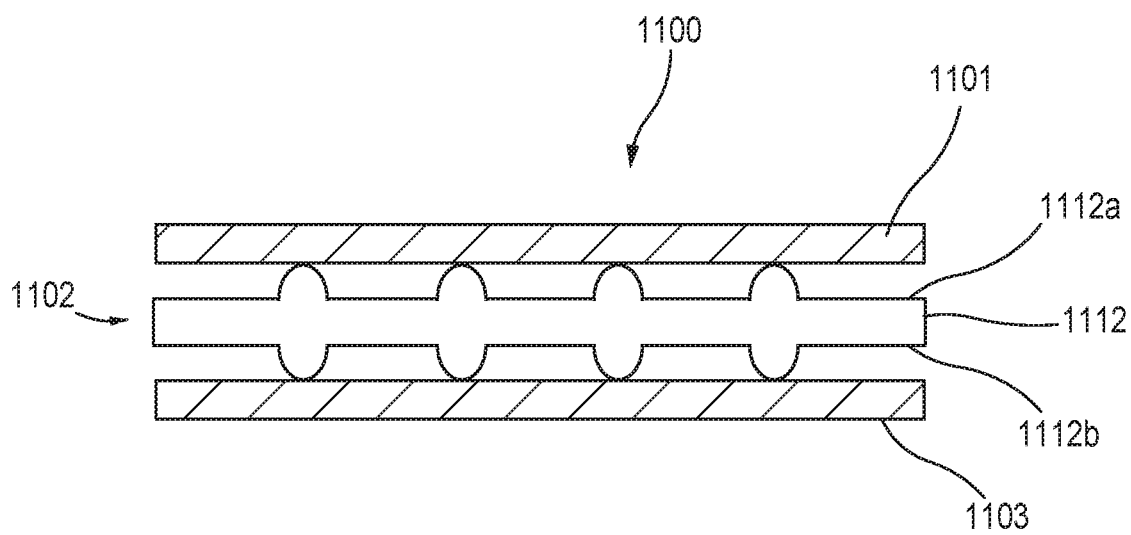
FIG. 14 illustrates a cross-section of an end view of a portion of an absorbent article according to an embodiment.
Figure 15:
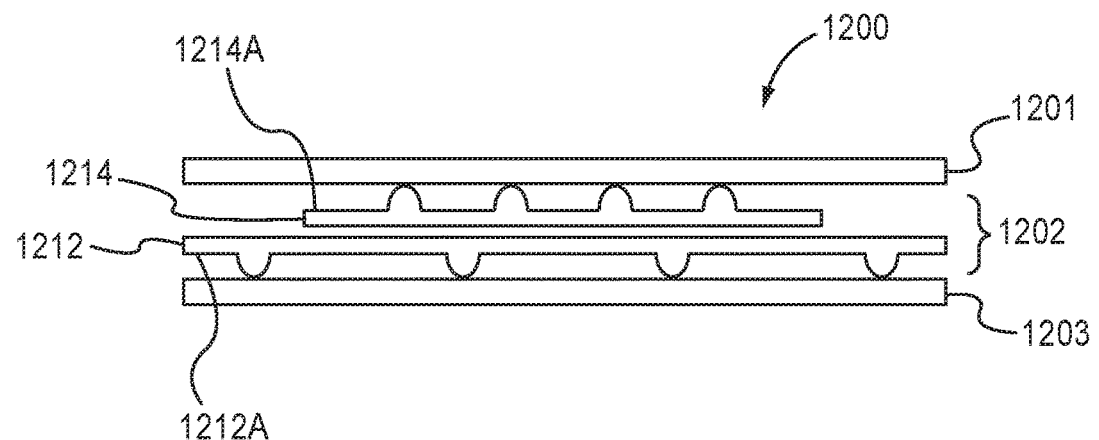
FIG. 15 illustrates a cross-section of an end view of a portion of an absorbent article according to an embodiment.

FIG. 14 is a cross-sectional view of a portion of an absorbent article 1100. The absorbent article 1100 can be similar to and include similar components with the absorbent article 1000. The absorbent article 1100 includes an inner layer 1101, an absorbent layer 1102, and an outer layer 1103. In general and applicable to any of the above embodiment, an absorbent layer 1102 may be positioned between the inner layer 1101 and the outer layer 1103 of the absorbent article. The absorbent layer 1102 includes a core 1112. Unlike the absorbent article 1000, the core 1112 includes and embossed top 1112A and an embossed bottom 1112B. In this manner, the core 1112 provides increased longitudinal movement of fluid on both the embossed top 1112A and embossed bottom 1112B of the core 1012, and reduced lateral flow, decreasing the potential for leaks from the side of the absorbent article 1100.

FIG. 12 is a cross-sectional end view of a portion of an absorbent article 1200. The absorbent article 1200 can be similar to and include similar components with the absorbent article 1000 and absorbent article 1100. The absorbent article 1200 includes an inner layer 1201, an absorbent layer 1202, and an outer layer 1203. In general and applicable to any of the above embodiment, the absorbent layer 1202 may be positioned between the inner layer 1201 and the outer layer 1203 of the absorbent article. The absorbent layer 1202 includes a first core 1212 and a second core 1214. Unlike the absorbent article 1000, but similar to absorbent article 100, the first core 1212 includes an embossed bottom 1212A and the second core 1214 includes an embossed top 1214A. In this manner, the first core 1212 and the second core 1212B provide increased longitudinal movement of fluid on both the embossed top 1214A and embossed bottom 1212B of the second core 1112 and the first core 1214, respectively.

Figure 16:
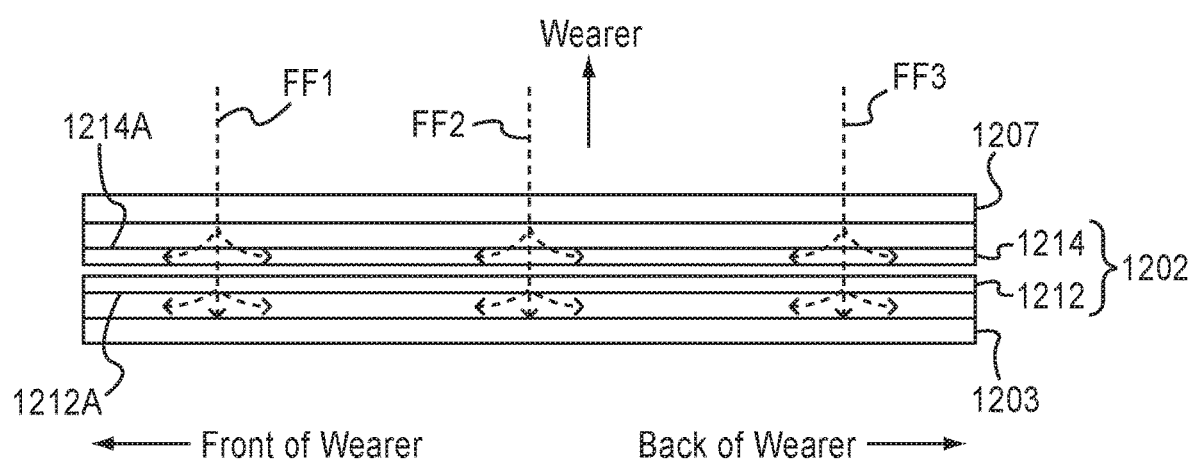
FIG. 16 illustrates a cross-section of a side view of a portion of the absorbent article shown in FIG. 15.

FIG. 16 is a side view of absorbent article 1200. As depicted in FIG. 16 fluid may flow from a wearer into contact with absorbent article 1200. Fluid flow is shown in FIG. 16 as dashed paths FF1, FF2, and FF3. While fluid flow is shown as dashed paths in FIG. 16, in some embodiments, fluid may not flow along a defined path, or paths, in any pattern, and may or may not contact absorbent article at any one or multiple particular locations. The fluid can first flow into contact with, be partially absorbed by, and pass through, inner layer 1201. The fluid can flow into contact with the embossed top 1214A of second core 1214. A portion of the fluid can be absorbed by second core 1214 and/or move longitudinally and/or laterally on and/or within second core 1214; and a portion of the fluid can pass through second core 1214 and into contact with first core 1212. Both the greater surface area of the embossed top 1214A, and the space created by embossed top 1214A between inner layer 1201 can direct the fluid flow longitudinally towards the front and the back of the wearer, and away from edges of absorbent article 1200 (e.g., reduced lateral flow. In this manner, when longitudinal flow is increased and/or when lateral flow is decreased, leakage can be reduced. A portion of the fluid can be absorbed by first core 1212 and/or move longitudinally and/or laterally on and/or within first core 1212; and a portion of the fluid can pass through first core 1212 and into contact with outer layer 1203. Both the greater surface area of the embossed bottom 1212A, and the space created by embossed bottom 1212A between outer layer 1203 can direct the fluid flow longitudinally towards the front and the back of the wearer, and away from edges of absorbent article 1200 (e.g., reduced lateral flow. In this manner, when longitudinal flow is increased and/or when lateral flow is decreased, leakage can be reduced.

FIGS. 17-25 illustrate a securement portion, also referred to as a side panel, 1304 for connection with a chassis 1302, the securement portion 1304 including a lamination layer 1350 incorporated therein. Securement portion 1304 can be similar to and include similar components with side panel securement portions 104, 106, 108, 110. Accordingly, features of the side panel 1304 may be incorporated into either a back securement portion or a front securement portion or both. However, it will be readily apparent to one of ordinary skill in the art that a side panel consistent with the examples shown in FIGS. 17-25 is not limited to the geometry of shown in these illustrative embodiments. Rather, one of ordinary skill will recognize that any of a broad variety of different side panel shapes, sizes and geometries may be appropriate.

Lamination layer 1350 may comprise a variety of different materials, including a combination of materials, that may provide various benefits as would be recognized by one of ordinary skill in the art. For example, lamination layer 1350 may comprise a high-loft nonwoven material to provide a softer side panel or an absorbent material to provide additional protection against leakage. Alternatively, the lamination layer may include one or more of the following materials: foam, airlaid, tissue, pulp, SAP, coform and meltblown material. In one embodiment, the lamination layer comprises a polypropylene or polyester nonwoven with a basis weight between 10 and 75 GSM, and more preferably 48 GSM.

Figure 17:
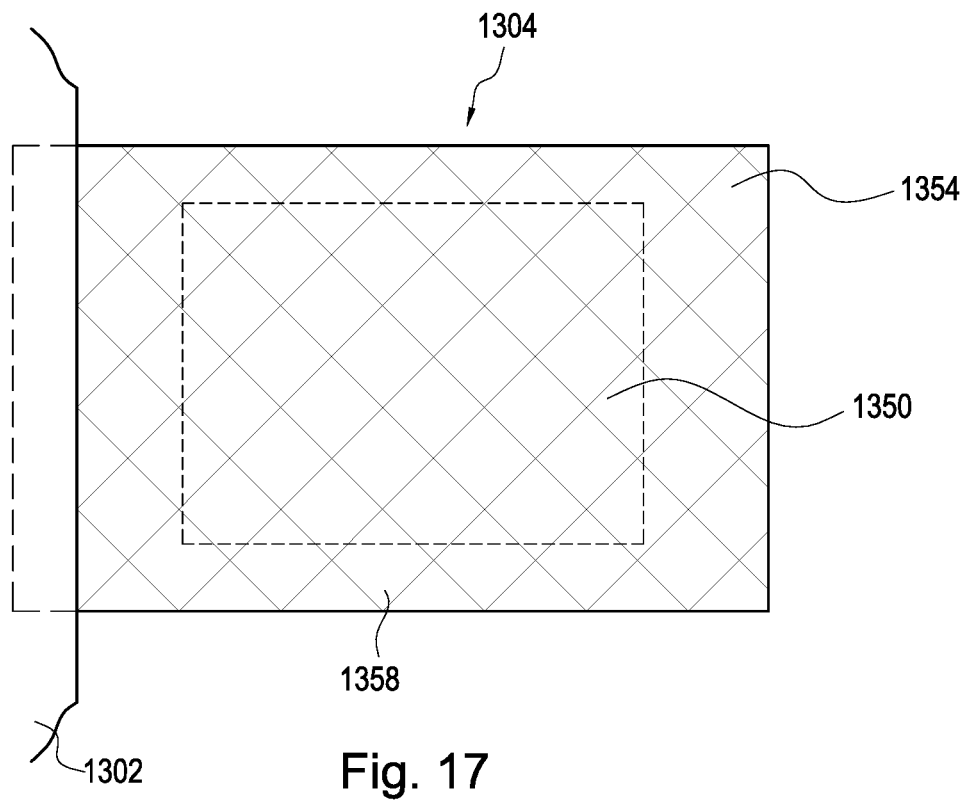
FIG. 17 illustrates a securement portion having a lamination layer according to one embodiment.
Figure 18:
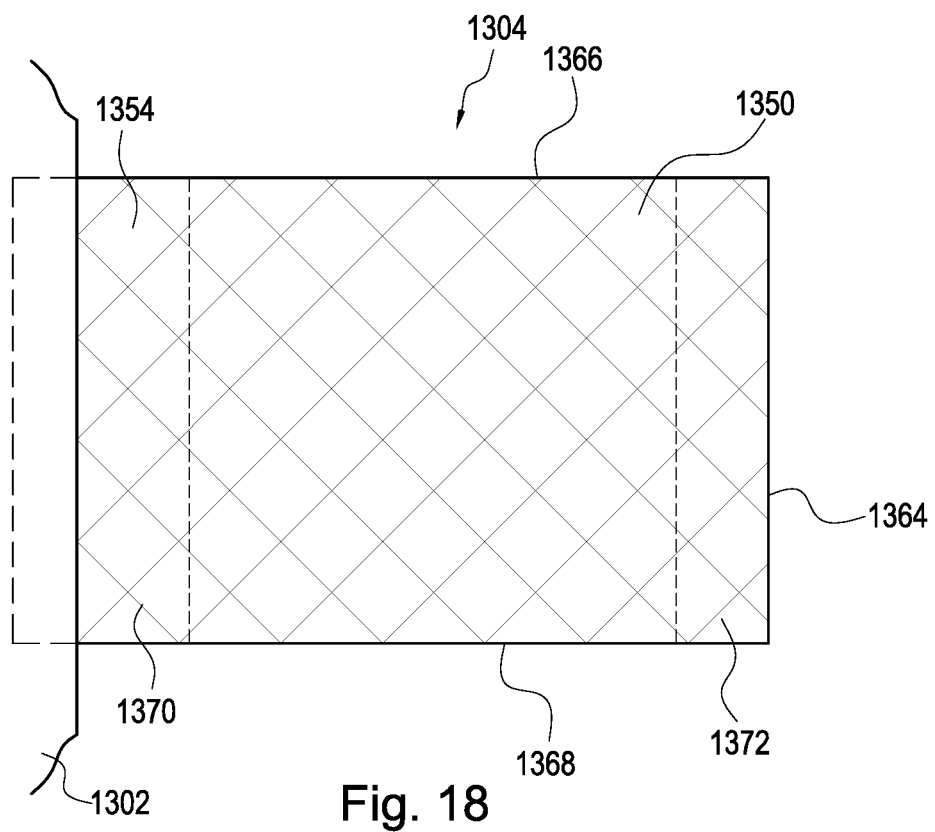
FIG. 18 illustrates a securement portion having a lamination layer according to a further embodiment.
Figure 20:
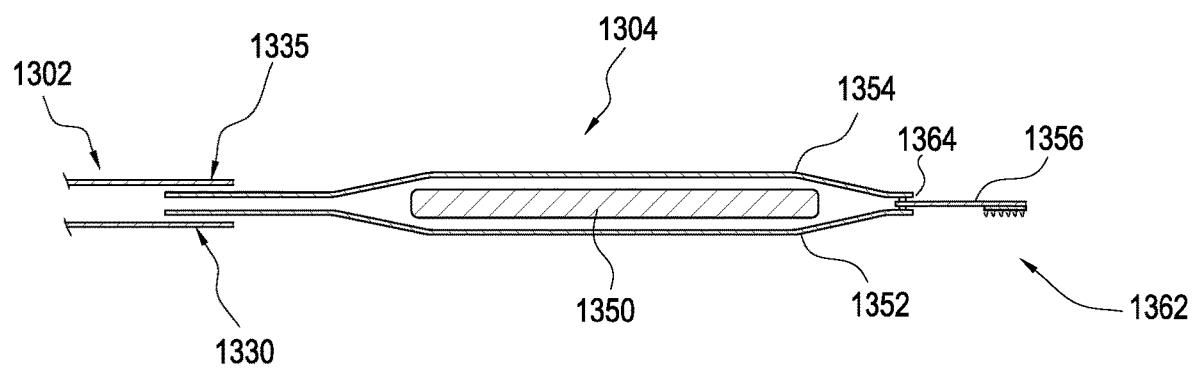
FIG. 20 illustrates a cross section of securement portion having a lamination layer according to the embodiment of FIG. 19.

In one embodiment, as illustrated by FIGS. 17 and 20, the side panel 1304 comprises a first outwardly facing layer 1354 and a second patient-facing layer 1352. A lamination layer 1350 may be positioned between the first 1354 facing layer and second 1352 facing layer. In a preferred embodiment, the lamination layer has a higher loft than either the patient-facing layer or outwardly facing layer. In addition, inclusion of the lamination layer 1350 in the side panel 1304 and the resulting laminate structure allows the use of materials for the facing layers 1352, 1354 that may not otherwise be appropriate for use without the lamination layer, such as softer or more flexible materials. In one embodiment, the facing layers comprise, for example, 10 to 20 GSM SMS nonwoven materials. Other appropriate facing layer materials may include spunbond or spunlaced nonwoven materials from polypropylene or polyethylene.

In the embodiment shown in FIG. 17, the lamination layer 1350 has a perimeter that is smaller than the perimeter of the first and second layers such that a portion 1358 of the side panel 1304 without a lamination layer completely surrounds the lamination layer. Alternatively, in the embodiment shown in FIG. 18, the lamination layer 1350 extents from a side panel top edge 1366 to a side panel bottom edge 1368 such that a first portion 1370 without a lamination layer is formed adjacent the chassis 1302 and a second portion 1372 without a lamination layer is formed adjacent the distal edge 1364 of the side panel. In a further embodiment, shown in FIGS. 21-22, alternating strips of lamination layer 1380*a*, 1380*b* 1380*c* are positioned between panel layers 1352, 1354. These strips 1380 may extend from panel top edge 1366 to panel bottom edge 1368. Alternatively, the strips may extend only part of the distance from top edge to bottom edge. It will be understood by one of ordinary skill in the art that, consistent with the present invention, the lamination layer may be arranged in any of a broad variety of continuous or intermittent layouts of which the embodiments discussed herein are only examples.

Figure 19:
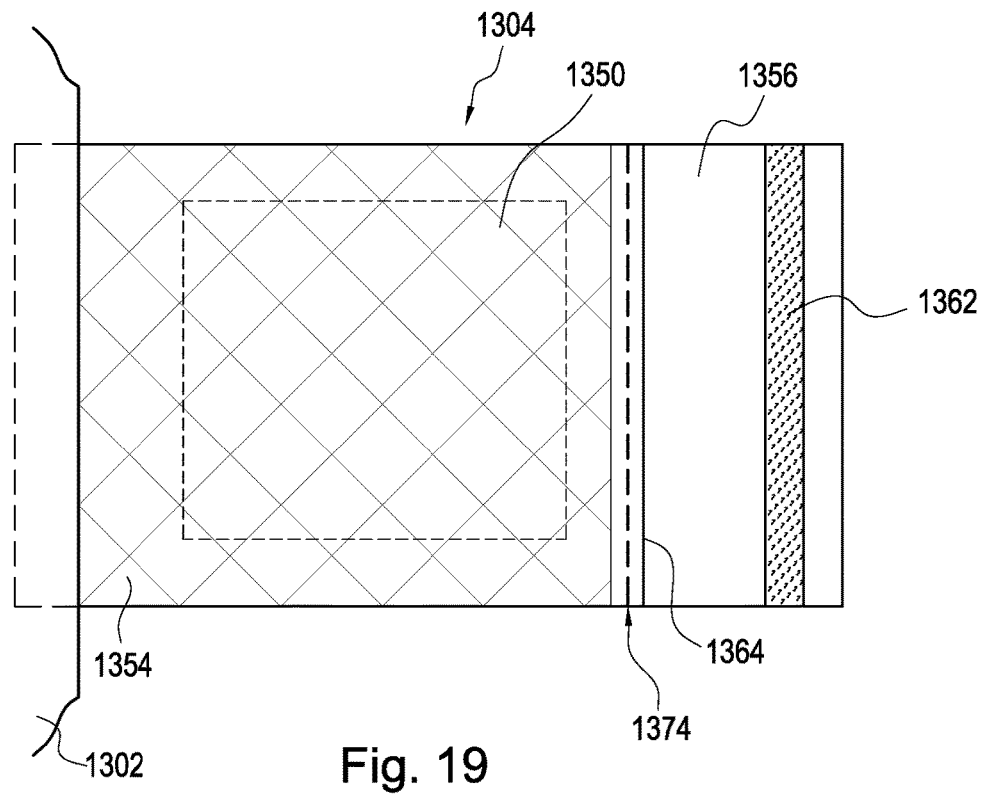
FIG. 19 illustrates a securement portion having a lamination layer according to a further embodiment.
Figure 21:
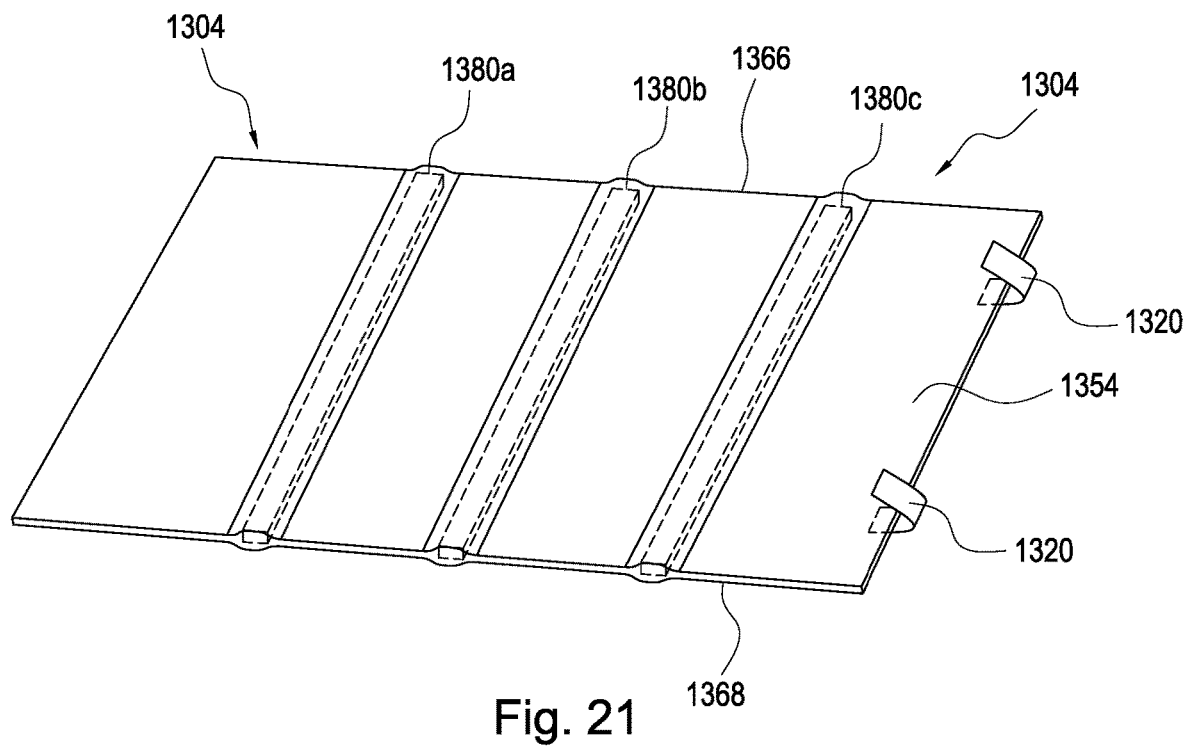
FIG. 21 illustrates a securement portion having a lamination layer according to a further embodiment.
Figure 22:
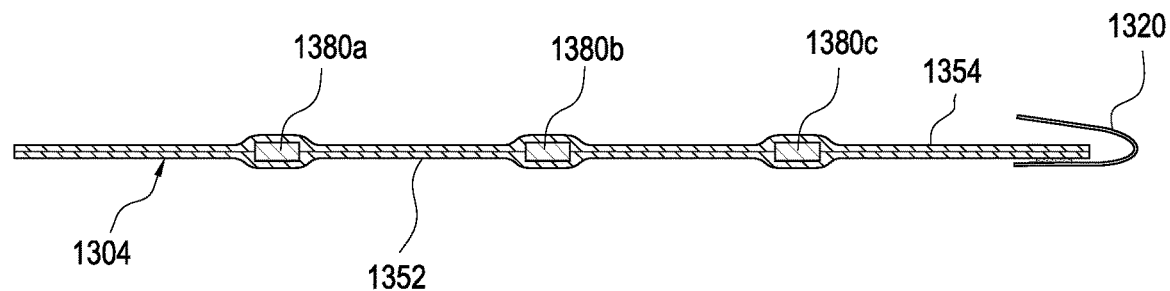
FIG. 22 illustrates a cross section of securement portion having a lamination layer according to the embodiment of FIG. 21.
Figure 23:
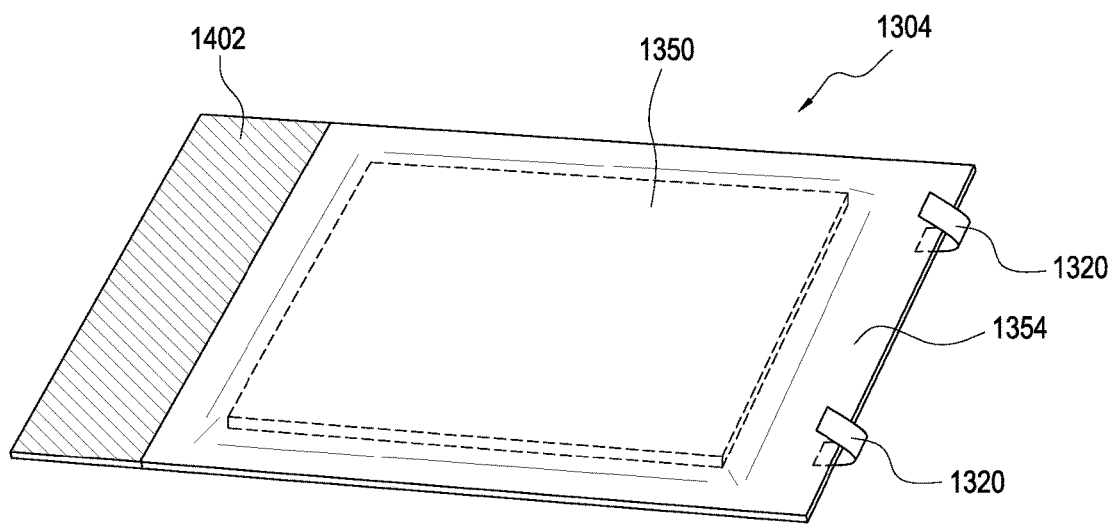
FIG. 23 illustrates a securement portion having a lamination layer according to a further embodiment.
Figure 24:
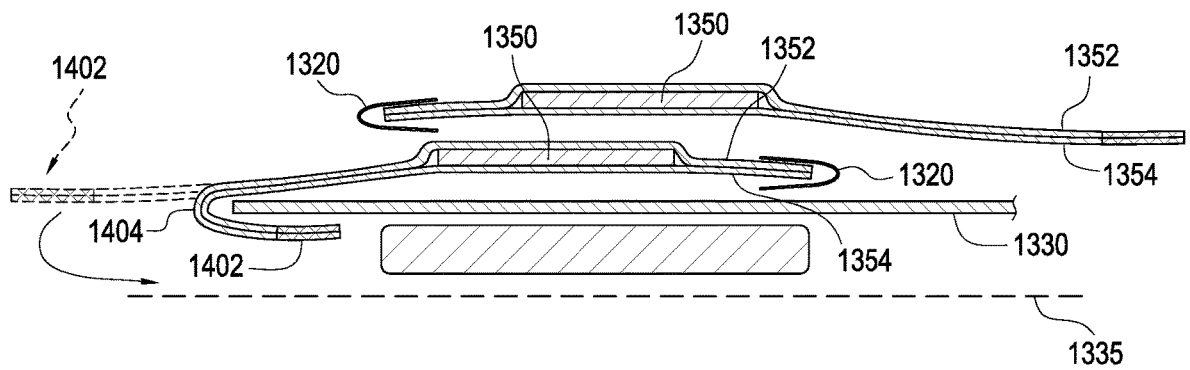
FIG. 24 illustrates a cross section of a folded absorbent article having a securement portion according to the embodiment of FIG. 23.

FIGS. 19-20 illustrate a further embodiment in which the side panel 1304 further incorporates an extension portion 1356 extending beyond the first and second layers 1352, 1354. This extension portion 1356 may comprise a stretchable material, such as an elastic panel. The extension may be glued or bonded 1374 along the distal edge 1364 of the side panel 1304. The extension may further comprise at least one fastener 1362 coupled thereto. This fastener 1362 may be the hook portion of a hook-and-loop fastener. Alternatively, as shown in FIGS. 21-22, the side panel 1304 may include fasteners 1320 similar to fasteners 120 as previously described with regard to FIG. 1.

As illustrated by FIG. 20, the side panel 1304 may be glued or bonded between an inner layer, or topsheet, 1330 and an outer layer, or backsheet, 1335 of the chassis 1302 in any manner that would be apparent to one of ordinary skill in the art.

Figure 25:
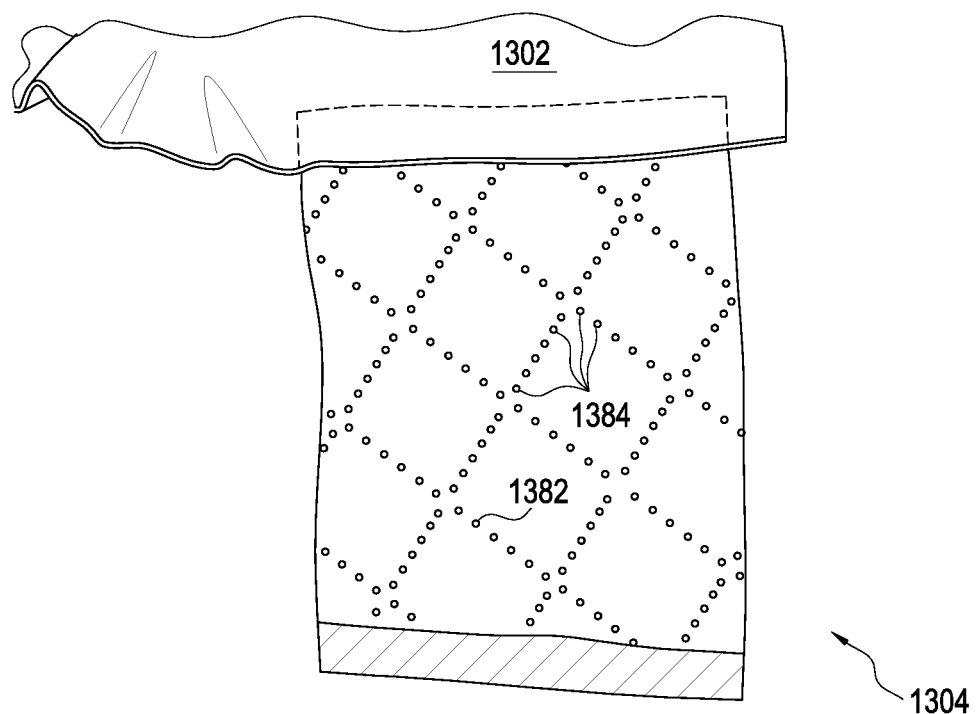
FIG. 25 illustrates an embodiment of a bonding pattern for a securement portion having a lamination layer.

The first layer 1354, lamination layer 1350 and second layer 1352 may be bonded by the use of glue, heat and pressure bonding, heat bonding alone, pressure bonding alone, or ultrasonic bonding methods. Bonding patterns can be created in a continuous mode or a patterned, registered manner. For example, FIG. 25 shows a side panel 1304 for attachment to a chassis 1302 as illustrated in FIG. 17. The side panel includes bonding pattern 1382 that creates a quilted appearance and/or feel for the side panel. The bonding pattern may be created by bonding one or more of the layers at a number of different bonding sites 1384. Other bonding patterns may also be used. In addition, the edges of the first and second layers 1354, 1352 may be bonded or sealed along the periphery of the side panel.

As illustrated by FIGS. 23-34, additional bonding 1402 may be performed after the time of laminating the lamination layer 1350 into the side panel 1304. This additional bonding can improve the process of applying and folding the product by virtue of creating a "fold line" 1404 in the side panel. This can be made to improve machine yield through reduced scrap, reduced inefficiency and reduction in out of spec products (folded side panels).

In an embodiment of the present invention, a skin care solution may be applied to the lamination layer 1350. The skin care solution may be absorbed by the lamination layer and then released onto the wearer's skin over a period of time. The skin care solution may be a lotion, gel, or other solution that could provide benefits to the wearer's skin, such as a reduction in irritation or ulcers. The skin care solution may include one or more ingredient known to promote healthy skin or prevent skin breakdown. Examples of such ingredients may include, but are not limited to, aloe vera, alpha hydroxy acids (including glycolic, lactic, malic, citric and tartaric acids), soy, grapeseed extract, vitamins A, C and E, coenzyme Q10, flavanoids, polyphenols, oat flour, honey, lactic acid, shea butter, petrolatum, lanolin, petrolatum, cyclomethicone, dimethicone copolyol, glyceryl stearates and propylene glycol linoleate, silicone, mineral oil, beeswax, caprylic/capric triglycerides, cyclomethicone, hydrogenated castor oil, mineral oil, lanolin, petroleum, petrolatum, silicone, dimethicone, vegetable oils, or any other ingredient know to improve skin condition. In further embodiments, a skin care solution may be applied to other absorbent portions of the absorbent article. For example, a skin care solution could be applied to one or more sections of the first absorbent core portion 116 or second absorbent core portion 118.

Figure 26:
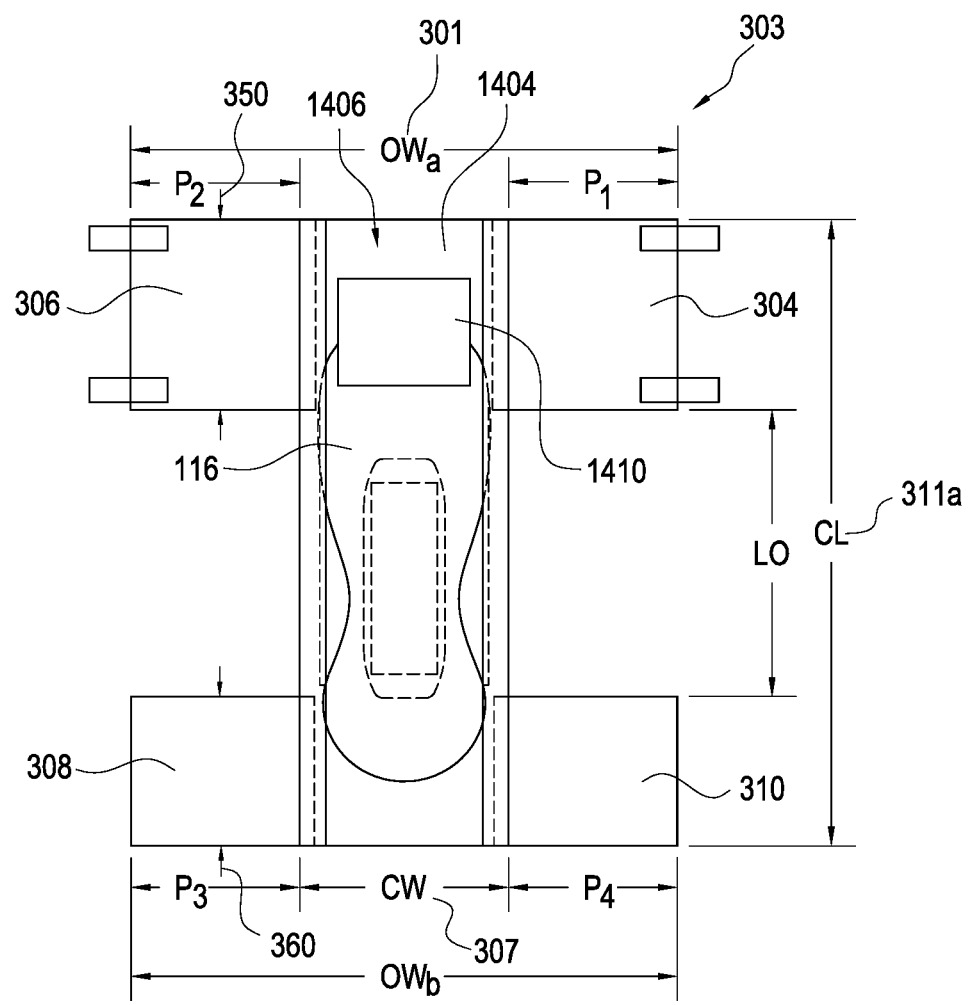
FIG. 26 illustrates a top view of an embodiment of an absorbent article including a sacral lamination layer.

As illustrated in FIG. 26, a further embodiment of the invention that may include a sacral lamination layer 1410 may be added to the inside surface 1404 of a rear portion 1406 of the chassis 1302. The sacral lamination layer may be positioned such that it is positioned adjacent a users sacral region, in vicinity of the intergluteal cleft and the tailbone, when wearing the absorbent article. This lamination layer 1410 may overlap with one or more other components that make up the chassis 1302, such as the first core portion 116. The sacral lamination layer may include a high-loft material that is affixed to the chassis topsheet 1330, by adhesive or other bonding means know to one of skill in the art. A further embodiment may include a patient facing layer positioned over the sacral lamination layer. The high-loft material and patient facing layer may be similar to those described above for use in side panel 1304. A skin care solution, such as described above, may be applied to the sacral lamination layer 1410.

The sacral lamination layer 1410 may have a variety of different shapes, including rectangular, oval, or "butterfly" shaped. In addition, the sacral lamination layer or sacral lamination layer and patient facing layer may include one or more of a variety of different embossing shapes or patterns as described herein or as would be known to one skilled in the art. Embodiments of the invention contemplate absorbent articles using both a lamination layer 1350 in side panel 1304 and a sacral lamination layer 1410. Alternatively side panel lamination layer or sacral lamination layer may be used independently.

Figure 27:
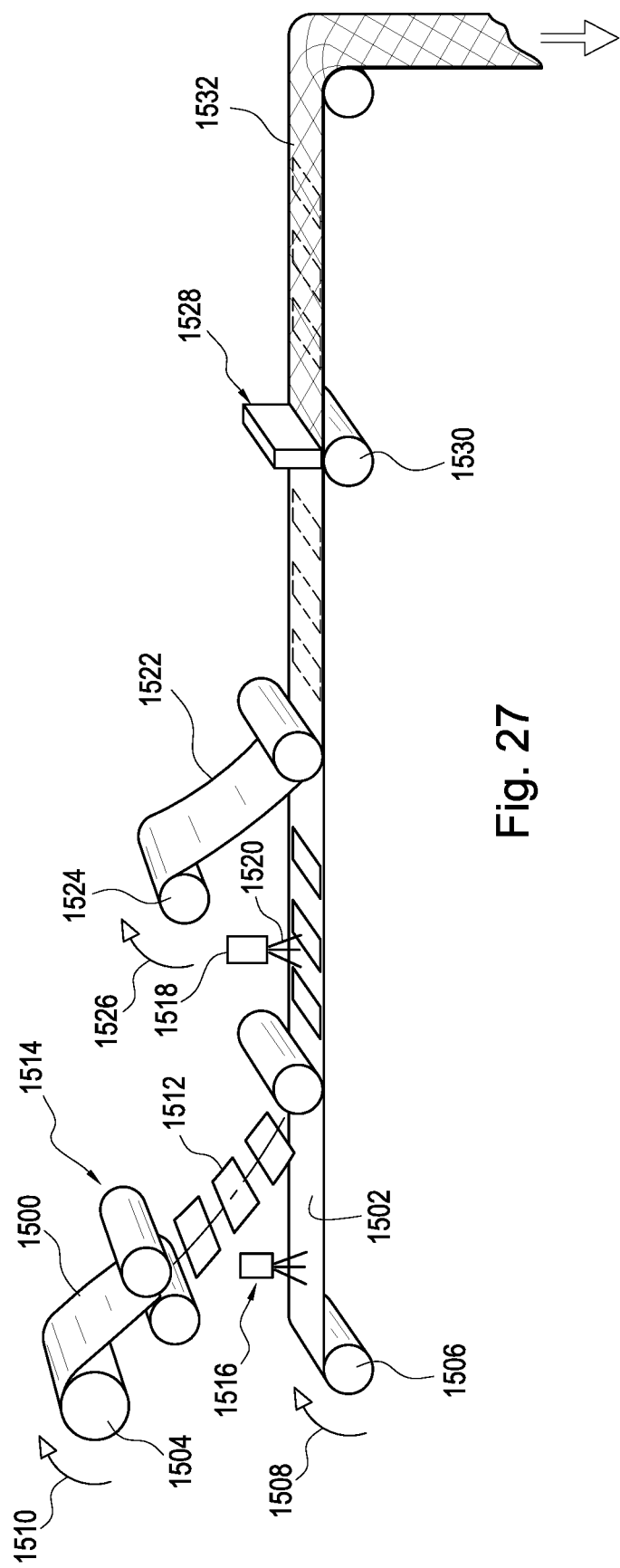
FIG. 27 illustrates a schematic of a portion an embodiment of a method for manufacturing an absorbent article with a rear side panel in accordance with embodiments shown in FIGS. 17-25.
Figure 28:
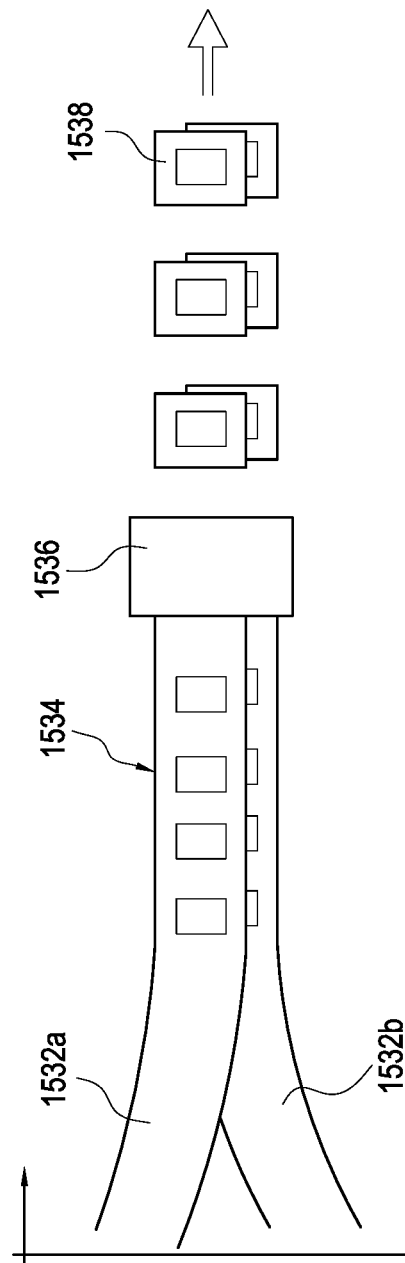
FIG. 28 illustrates a schematic of a further portion an embodiment of a method for manufacturing an absorbent article with a rear side panel in accordance with embodiments shown in FIGS. 17-25.
Figure 29:
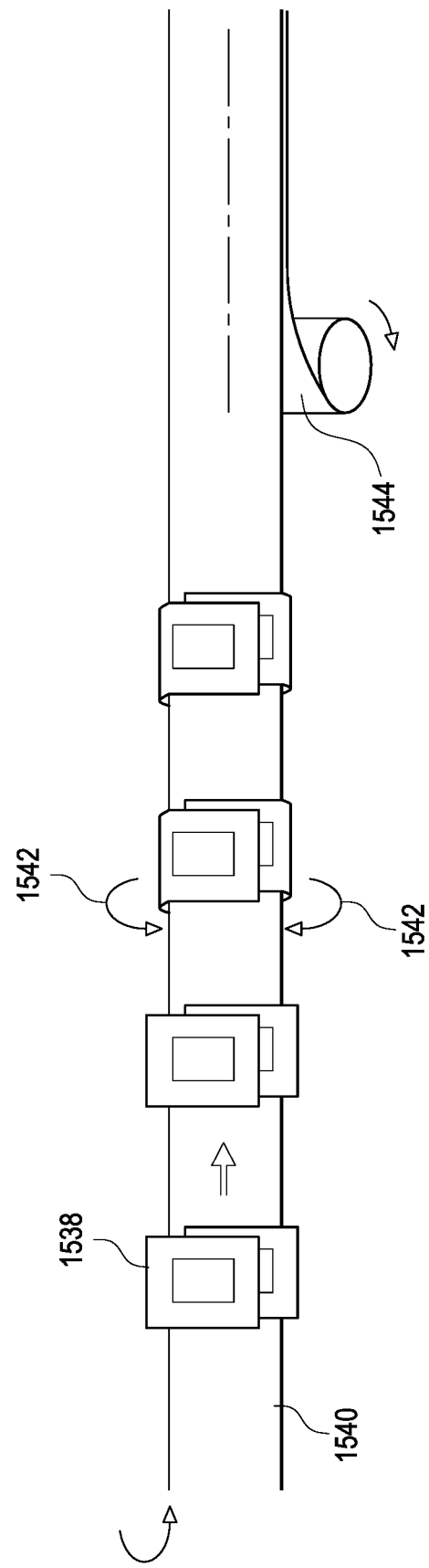
FIG. 29 illustrates a schematic of a further portion an embodiment of a method for manufacturing an absorbent article with a rear side panel in accordance with embodiments shown in FIGS. 17-25.

FIGS. 27-29 illustrate embodiments of a method for manufacturing an absorbent article with a rear side panel 1304 in accordance with embodiments shown in FIGS. 17-25. Embodiments of the manufacturing method may include the following steps: (1) Unwind a continuous web 1502 first facing layer 1354 of a side panel 1304 from a roll 1506 of facing material in a direction indicated by arrow 1508. (2) Unwind a continuous web 1500 of first lamination layer 1350 for the side panel from a roll 1504 of facing material in a direction indicated by arrow 1510. (3) Provide a short piece 1512 of lamination layer by feeding the lamination layer through a slip and cut 1514 (also known to those of skill in the art as cut and place) can also be performed with a cutting unit followed by a placing unit—as driven by either mechanical cam or servo motor unit, thereby providing an intermittent patch 1512 of lamination layer 1350 onto a continuous web of the first facing layer 1354 of the side panel 1304. This process may require adhesive 1516 to be applied to the first facing layer 1502. The slip/cut applicator may also require vacuum in order to hold the lamination layer within the unit until severed, accelerated and glued in place to the first facing layer. (4)

Apply skin care lotion 1520 to the lamination layer piece 1512 through intermittent application using a spray applicator 1518, extrusion die, rotary gravure printing, or other applicator process. (5) Unwind a continuous web 1522 of second facing layer 1352 of side panel material from a roll 1524 of facing material in a direction indicated by arrow 1526. (6) Marry the first facing layer 1502 (with intermittent lamination layer patches 1512) with the second facing layer 1522. (7) Feed the combined layers through an ultrasonic bonding unit 1528, or a heated calendaring unit (also known as heat and pressure bonding unit), including a pattern roll 1530, to provide a quilted lamination pattern 1382 (or other, aesthetically pleasing pattern) which traps the lamination layer between the facing layers and provides an appearance of softness. (Hotmelt adhesive lamination can also be utilized for this application, but without benefit of a quilted bonding appearance) (8) Using the same pattern roll 1530, or a second means (which could be another ultrasonic bonding unit or a pressure unit, or a heated unit), provide a bonding pattern 1402 on the edges of the side panel 1304. (9) Add tape tabs 120 to the panel assemblies (not shown). An alternative to tape tabs as shown would be a continuous hook, a hook strip 1362 that is shorter than the panel assembly, or a plurality of hook strips that can be used to preferentially attach the side panel 1304 to either a corresponding side panel, or the front of the product's chassis 1302. Embodiments of the portion of the manufacturing process shown in FIG. 27 create a continuous panel web 1532.

FIG. 28 illustrates an embodiment of a further portion of the manufacturing process, including the following steps: (10) Provide a first continuous panel web 1532a and a second continuous panel web 1532b. The two panel webs 1532a, 1532b are overlapped in a slightly offset manner 1534. (11) A cutoff and spacing unit 1536 severs and spaces the panel webs into discrete pairs 1538 of side panels 1304.

As illustrated in FIG. 29, an embodiment of a further portion of the manufacturing process includes the following steps: (12) Place the discrete pairs 1538 of side panels 1304 onto a continuous web 1540 of topsheet 1330 material. (13) Fold an edge of each side panel 1304 under the topsheet web 1540 along fold line 1404 as shown by arrows 1542. (14) Marry a continuous web 1544 of backsheet 1335 material, combined with absorbent cores, to the continuous web 1540 or the topsheet. (15) Adhere an edge of each side panel 1304 between the topsheet 1330 and the backsheet 1335, as illustrated in FIG. 20. In an alternate embodiment of this process, further side panels are manufactured without the tape tabs for use in a front side panel application.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. By way of example, any of the absorbent articles described herein can include any of the absorbent layers described in FIGS. 10-12. Each of these embodiments and obvious variations thereof is contemplated as falling within the spirit and scope of the invention, which is set forth in the following alternative embodiments.

What is claimed is:

1. A method of manufacturing a first absorbent article having a first size and a second absorbent article having a second size, the method comprising the steps of:
    assembling the first absorbent article by:
        forming a first chassis comprising:
            a first chassis length extending in a longitudinal direction from the back to the front of a user,
            a first chassis width extending in a lateral direction substantially perpendicular to the length between first and second longitudinal edges,
            a front waist region,
            a back waist region, and
            a crotch region extending between the front waist region and the back waist region;
        attaching a first panel to the back waist region of the first chassis, the first panel comprising:
            a first panel width extending in a lateral direction from the first longitudinal edge of the first chassis, and
            a first panel length extending longitudinally along the first longitudinal edge of the first chassis;
    assembling the second absorbent article by:
    forming a second chassis comprising:
        a second chassis length extending in a longitudinal direction from the back to the front of a user, wherein the second chassis length is greater than the first chassis length,
        a second chassis width extending in a lateral direction substantially perpendicular to the length between first and second longitudinal edges, wherein the second chassis width is substantially the same as the first chassis width,
        a front waist region,
        a back waist region, and
        a crotch region extending between the first and second portion;
    attaching a second panel to the back waist region of the second chassis, the second panel comprising:
        a second panel width extending in a lateral direction from the first longitudinal edge of the second chassis, and
        a second side panel length extending longitudinally along the first longitudinal edge of the second chassis.

2. The method of claim 1, wherein the second panel width is greater than the first panel width.

3. The method of claim 2, wherein the second panel length is substantially the same as the first panel length.

4. The method of claim 2, wherein the second panel length is greater than the first panel length.

5. The method of claim 1, wherein assembling the first absorbent article further comprises the step of attaching a first fastener to the first panel at a position spaced apart from the first longitudinal edge of the first chassis.

6. The method of claim 5, wherein assembling the second absorbent article further comprises the step of attaching a second fastener to the second panel at a position spaced apart from the first longitudinal edge of the second chassis.

7. The method of claim 1, wherein assembling the first absorbent article further comprises attaching a third panel to the back waist region of the first chassis, the third panel comprising:
    a third panel width extending in a lateral direction from the second longitudinal edge of the first chassis, and
    a third panel length extending longitudinally along the second longitudinal edge of the first chassis.

8. The method of claim 7, wherein assembling the second absorbent article further comprises attaching a fourth panel to the back waist region of the second chassis, the first panel comprising:
    a fourth panel width extending in a lateral direction from the second longitudinal edge of the second chassis, and a fourth panel length extending longitudinally along the second longitudinal edge of the second chassis.

9. A method of manufacturing a first absorbent article having a first size and a second absorbent article having a second size, the method comprising the steps of:
assembling the first absorbent article using an assembly machine implementing steps comprising:
forming a first chassis having a first chassis length extending in a longitudinal direction from the back to the front of a user and a first chassis width extending in a lateral direction substantially perpendicular to the length;
attaching a first side panel to the first chassis, the first side panel having a first side panel width extending in the lateral direction and a first side panel length extending in the longitudinally direction;
assembling the second absorbent article using an assembly machine implementing steps comprising:
forming a second chassis having a second chassis length extending in a longitudinal direction from the back to the front of a user and the first chassis width extending in a lateral direction substantially perpendicular to the length;
attaching a second side panel to the second chassis, the second side panel having a second side panel width extending in the lateral direction and a second side panel length extending in the longitudinally direction.

10. The method of claim 9, wherein the step of forming the first chassis comprises the steps of:
unwinding a continuous web of topsheet material;
unwinding a continuous web of backsheet material; and
marrying the topsheet material to the backsheet material to form a continuous web of chassis material.

11. The method of claim 10, wherein the step of attaching the first side panel to the first chassis comprises the steps of:
unwinding a continuous web of a side panel material; and
severing the continuous web of side panel material to form a first side panel having the first side panel width.

12. The method of claim 11, wherein the step of attaching the first side panel to the first chassis comprises attaching an edge of the first side panel to the first chassis at a first chassis longitudinal edge.

13. The method of claim 12, the step of attaching the first side panel to the first chassis comprises positioning the edge of the first side panel between the topsheet and the backsheet at the first chassis longitudinal edge.

14. The method of claim 12, wherein the step of forming the first chassis further comprises cutting the continuous web of chassis material to form a first chassis having the first chassis length and the first chassis width.

15. The method of claim 14, wherein the step of forming the second chassis comprises the steps of:
unwinding the continuous web of topsheet material;
unwinding the continuous web of backsheet material;
marrying the topsheet material to the backsheet material to form the continuous web of chassis material; and
cutting the continuous web of chassis material to form a second chassis having the second chassis length and the first chassis width.

16. The method of claim 15, wherein the step of attaching the second side panel to the second chassis comprises the steps of:
unwinding a continuous web of a side panel material;
severing the continuous web of side panel material to form a second side panel having the second side panel width; and
attaching an edge of the second side panel to the second chassis at a second chassis longitudinal edge.

17. A method of manufacturing a first absorbent article having a first size and a second absorbent article having a second size, the method comprising the steps of:
extending a portion of a continuous web of topsheet material;
extending a portion of a continuous web of backsheet material;
extending a portion of a continuous web of first side panel material;
severing the continuous web of first side panel material to form a first side panel having a first side panel width;
inserting an edge of the first side panel between the continuous web of topsheet material and the continuous web of backsheet material with a section of the first side panel extending in a lateral direction beyond a longitudinal edge of the topsheet and backsheet continuous webs;
marrying the topsheet material to the backsheet material to form a continuous web of chassis material;
cutting the continuous web of chassis material to form a first chassis having a first chassis length and a first chassis width;
extending a further portion of the continuous web of topsheet material;
extending a further portion of the continuous web of backsheet material;
extending a portion of a continuous web of a second side panel material;
severing the continuous web of second side panel material to form a second side panel having a second side panel width that is greater than the first side panel width;
inserting an edge of the second side panel between the continuous web of topsheet material and the continuous web of backsheet material with a section of the second side panel extending in the lateral direction beyond the longitudinal edge of the topsheet and backsheet continuous webs;
marrying the topsheet material to the backsheet material to form the continuous web of chassis material; and
cutting the continuous web of chassis material to form a second chassis having a second chassis length and the first chassis width.

18. The method of claim 17 further comprising the step attaching the edge of the first side panel to the topsheet material and the backsheet material.

19. The method of claim 18, wherein the step of attaching the edge of the first side panel to the topsheet material and the backsheet material comprises adhering the edge of the first side panel to the topsheet material and the backsheet material using an adhesive.

20. The method of claim 18, wherein the step of attaching the edge of the first side panel to the topsheet material and the backsheet material comprises bonding the edge of the first side panel to the topsheet material and the backsheet material using an ultrasonic bond.

21. The method of claim 17, wherein:
the step of cutting the continuous web of chassis material to form the first chassis comprises cutting the continuous web of chassis material with a cutting die;
the step of cutting the continuous web of chassis material to form the second chassis comprises cutting the continuous web of chassis material with the cutting die;
and the cutting die is not replaced between the step of cutting the continuous web of chassis material to form the first chassis and the step of cutting the continuous web of chassis material to form the second chassis.

* * * * *